(12) United States Patent
Lee et al.

(10) Patent No.: US 10,945,968 B2
(45) Date of Patent: Mar. 16, 2021

(54) MEMANTINE TRANSDERMAL DELIVERY SYSTEMS

(71) Applicant: Corium, Inc., Menlo Park, CA (US)

(72) Inventors: Eun Soo Lee, Redwood City, CA (US); Parminder Singh, Union City, CA (US); Appala Sagi, Mountain View, CA (US); Amit K. Jain, Milpitas, CA (US)

(73) Assignee: Corium, Inc., Grand Rapids, MI (US)

( * ) Notice: Subject to any disclaimer, the term of this patent is extended or adjusted under 35 U.S.C. 154(b) by 267 days.

(21) Appl. No.: 15/660,929

(22) Filed: Jul. 26, 2017

(65) Prior Publication Data

US 2018/0028466 A1   Feb. 1, 2018

Related U.S. Application Data

(60) Provisional application No. 62/504,391, filed on May 10, 2017, provisional application No. 62/457,794, filed on Feb. 10, 2017, provisional application No. 62/457,791, filed on Feb. 10, 2017, provisional application No. 62/444,763, filed on Jan. 10, 2017, provisional application No. 62/444,745, filed on Jan. 10, 2017, provisional application No. 62/423,133, filed on Nov. 16, 2016, provisional application No. 62/367,502, filed on Jul. 27, 2016.

(51) Int. Cl.
| | |
|---|---|
| *A61K 9/70* | (2006.01) |
| *A61K 31/13* | (2006.01) |
| *A61K 31/045* | (2006.01) |
| *A61K 9/00* | (2006.01) |
| *A61K 47/16* | (2006.01) |

(52) U.S. Cl.
CPC .......... *A61K 9/7084* (2013.01); *A61K 9/7038* (2013.01); *A61K 9/7061* (2013.01); *A61K 9/7092* (2013.01); *A61K 31/045* (2013.01); *A61K 31/13* (2013.01); *A61K 9/0014* (2013.01); *A61K 47/16* (2013.01)

(58) Field of Classification Search
None
See application file for complete search history.

(56) References Cited

U.S. PATENT DOCUMENTS

| | | | |
|---|---|---|---|
| 3,391,142 A | 7/1968 | Mills et al. | |
| 3,546,141 A | 12/1970 | Washburn et al. | |
| 3,549,016 A | 12/1970 | Rigopulos | |
| 4,122,193 A | 10/1978 | Scherm et al. | |
| 4,273,774 A | 6/1981 | Scherm | |
| 4,781,924 A | 11/1988 | Lee et al. | |
| 4,837,027 A | 6/1989 | Lee et al. | |
| 4,849,224 A | 7/1989 | Chang et al. | |
| 4,880,633 A | 11/1989 | Loper et al. | |
| 4,886,812 A | 12/1989 | Griss et al. | |
| 4,895,841 A | 1/1990 | Sugimoto et al. | |
| 5,026,556 A | 6/1991 | Drust et al. | |
| 5,061,703 A | 10/1991 | Bormann et al. | |
| 5,123,900 A | 6/1992 | Wick | |
| 5,252,588 A | 10/1993 | Azuma et al. | |
| 5,424,077 A | 6/1995 | Lajoie | |
| 5,614,560 A | 3/1997 | Lipton | |
| 5,635,203 A | 6/1997 | Gale et al. | |
| 5,662,925 A | 9/1997 | Ebert et al. | |
| 5,866,585 A | 2/1999 | Fogel | |
| 5,958,919 A | 9/1999 | Olney et al. | |
| 6,004,578 A | 12/1999 | Lee et al. | |
| 6,255,348 B1 | 7/2001 | Elstner | |
| 6,383,471 B1 | 5/2002 | Chen et al. | |
| 6,512,010 B1 | 1/2003 | Gale et al. | |
| 6,521,639 B1 | 2/2003 | Murahashi et al. | |
| 6,746,689 B2 | 6/2004 | Fischer et al. | |
| 6,923,988 B2 | 8/2005 | Patel et al. | |
| 6,929,801 B2 | 8/2005 | Klose et al. | |
| 7,097,853 B1 | 8/2006 | Garbe et al. | |
| 7,176,185 B2 | 2/2007 | Hilfinger et al. | |

(Continued)

FOREIGN PATENT DOCUMENTS

| | | |
|---|---|---|
| CN | 102048678 A | 5/2011 |
| CN | 105693556 A | 6/2016 |

(Continued)

OTHER PUBLICATIONS

US 9,095,635 B1, 08/2015, Willmann et al. (withdrawn)
International Search Report from International Patent Application No. PCT/US2018/043961, 6 pages, dated Nov. 23, 2018.
International Search Report from International Patent Application No. PCT/US2017/038934 dated Oct. 10, 2017.
Del Rio-Sancho et al., "Transdermal therapeutic systems for memantine delivery. Comparison of passive and iontophoretic transport", Int. J. Pharm., vol. 517, No. 1-2, pp. 104-111 (2017).
International Search Report from International Patent Application No. PCT/US2018/066848, 7 pages, dated Apr. 15, 2019.
Mittapelly et al., "In Depth Analysis of Pressure-Sensitive Adhesive Patch-Assisted Delivery of Memantine and Donepezil Using Physiologically Based Pharmacokinetic Modeling and in Vitro/in Vivo Correlations", Mol. Pharm., vol. 15, No. 7, pp. 2646-2655 (2018).

(Continued)

*Primary Examiner* — David J Blanchard
*Assistant Examiner* — Daniel F. Coughlin
(74) *Attorney, Agent, or Firm* — McDermott, Will & Emery LLP; Judy M. Mohr

(57) ABSTRACT

Transdermal delivery systems for the systemic delivery of memantine are described, wherein the system comprises a drug reservoir layer and an adhesive layer, optionally together with one or more intermediate and/or supporting layers, wherein the drug reservoir layer comprises an acrylate polymer or copolymer, a permeation enhancer, a carrier, and memantine base generated in situ by reaction of a memantine salt and an alkaline salt. Compositions and kits comprising the various components, e.g., drug reservoir and/or adhesive compositions are described. Methods relating to treatment of CNS disorders, e.g., Alzheimer's disease and/or dementia, using the aforementioned transdermal delivery devices and/or compositions are also described.

17 Claims, 2 Drawing Sheets

(56) References Cited

U.S. PATENT DOCUMENTS

| | | | |
|---|---|---|---|
| 7,250,394 B2 | 7/2007 | Nedergaard | |
| 7,320,802 B2 | 1/2008 | Ryde et al. | |
| 7,335,379 B2 | 2/2008 | Carrara et al. | |
| 7,462,743 B2 | 12/2008 | Merli et al. | |
| 7,670,838 B2 | 3/2010 | Deisseroth et al. | |
| 7,682,628 B2 | 3/2010 | Singh | |
| 7,744,918 B2 | 6/2010 | Yamaguchi et al. | |
| 7,858,114 B2 | 12/2010 | Ito | |
| 7,888,422 B2 | 2/2011 | Jackson et al. | |
| 8,058,291 B2 | 11/2011 | Went et al. | |
| 8,168,209 B2 | 5/2012 | Went et al. | |
| 8,246,978 B2 | 8/2012 | Kydonieus et al. | |
| 8,252,321 B2 | 8/2012 | Dipierro et al. | |
| 8,283,379 B2 | 10/2012 | Went et al. | |
| 8,362,085 B2 | 1/2013 | Went et al. | |
| 8,512,742 B2 | 8/2013 | Amano et al. | |
| 8,614,274 B2 | 12/2013 | Jackson et al. | |
| 8,673,338 B2 | 3/2014 | Bleier | |
| 8,784,879 B2 | 7/2014 | Singh et al. | |
| 8,815,281 B2 | 8/2014 | Kanios et al. | |
| 8,840,922 B2 | 9/2014 | Kawakami et al. | |
| 8,840,935 B2 | 9/2014 | Haber et al. | |
| 8,874,879 B2 | 10/2014 | Ge et al. | |
| 9,012,511 B2 | 4/2015 | Neville et al. | |
| 9,248,104 B2 | 2/2016 | Valia et al. | |
| 9,622,986 B2 | 4/2017 | Im et al. | |
| 9,993,466 B2 | 6/2018 | Lee et al. | |
| 10,016,372 B2 | 7/2018 | Singh et al. | |
| 10,300,025 B2 | 5/2019 | Lee et al. | |
| 10,307,379 B2 | 6/2019 | Lee et al. | |
| 2001/0031787 A1 | 10/2001 | Hsu et al. | |
| 2002/0192243 A1 | 12/2002 | Hsu et al. | |
| 2003/0170308 A1 | 9/2003 | Cleary et al. | |
| 2004/0022835 A1 | 2/2004 | Pai et al. | |
| 2004/0033254 A1 | 2/2004 | Song et al. | |
| 2004/0087658 A1 | 5/2004 | Moebius | |
| 2005/0113458 A1 | 5/2005 | Gupta et al. | |
| 2006/0035888 A1 | 2/2006 | Jonas et al. | |
| 2006/0205822 A1 | 9/2006 | Jonas et al. | |
| 2008/0038328 A1 | 2/2008 | Higo et al. | |
| 2008/0107719 A1 | 5/2008 | Likitlersuang et al. | |
| 2008/0131490 A1 | 6/2008 | Hanatani et al. | |
| 2008/0131491 A1 | 6/2008 | Hanatani et al. | |
| 2008/0138388 A1 | 6/2008 | Aida et al. | |
| 2009/0081259 A1 | 3/2009 | Jonas et al. | |
| 2009/0124659 A1 | 5/2009 | Moebius | |
| 2009/0156639 A1 | 6/2009 | Trippodi-Murphy et al. | |
| 2009/0175929 A1 | 7/2009 | Terahara et al. | |
| 2009/0291127 A1 | 11/2009 | Wen et al. | |
| 2010/0121290 A1 | 5/2010 | Rasmussen et al. | |
| 2010/0178037 A1 | 7/2010 | Chen et al. | |
| 2010/0227852 A1 | 9/2010 | Moebius | |
| 2010/0291186 A1 | 11/2010 | Singh et al. | |
| 2011/0059141 A1 | 3/2011 | Ito | |
| 2011/0059169 A1 | 3/2011 | Went et al. | |
| 2011/0066120 A1 | 3/2011 | Lee | |
| 2011/0244023 A1 | 10/2011 | Cottrell et al. | |
| 2011/0313372 A1 | 12/2011 | Eifler et al. | |
| 2012/0121729 A1* | 5/2012 | Paterson | A61K 45/06 424/670 |
| 2012/0245537 A1 | 9/2012 | Horstmann et al. | |
| 2013/0053358 A1 | 2/2013 | Aida et al. | |
| 2014/0052081 A1 | 2/2014 | Yang et al. | |
| 2014/0256690 A1 | 9/2014 | Arkady et al. | |
| 2014/0322284 A1 | 10/2014 | Singh et al. | |
| 2014/0370076 A1 | 12/2014 | Choi et al. | |
| 2015/0098980 A1 | 4/2015 | Pongpeerapat et al. | |
| 2016/0051486 A1 | 2/2016 | Choi et al. | |
| 2017/0202830 A1 | 7/2017 | Stinchcomb et al. | |
| 2017/0360908 A1* | 12/2017 | Shishido | A61K 38/00 |
| 2018/0028461 A1 | 2/2018 | Singh et al. | |
| 2018/0028462 A1 | 2/2018 | Lee et al. | |
| 2018/0028463 A1 | 2/2018 | Lee et al. | |
| 2018/0028467 A1 | 2/2018 | Singh et al. | |
| 2018/0028512 A1 | 2/2018 | Lee et al. | |
| 2018/0028663 A1 | 2/2018 | Lee et al. | |
| 2018/0185298 A1 | 7/2018 | Jain et al. | |
| 2018/0235901 A1 | 8/2018 | Lee et al. | |
| 2019/0029971 A1 | 1/2019 | Lee et al. | |

FOREIGN PATENT DOCUMENTS

| | | |
|---|---|---|
| EP | 0296560 A2 | 12/1988 |
| EP | 0540623 B1 | 9/1994 |
| EP | 1423100 A1 | 6/2004 |
| EP | 1682109 B1 | 10/2008 |
| EP | 2016941 A1 | 1/2009 |
| EP | 2090310 A1 | 8/2009 |
| EP | 2098233 A1 | 9/2009 |
| EP | 2098235 A1 | 9/2009 |
| EP | 2260839 A2 | 12/2010 |
| EP | 2514415 A1 | 10/2012 |
| EP | 2638906 A1 | 9/2013 |
| EP | 2818161 A1 | 12/2014 |
| JP | H06-199659 A | 7/1994 |
| JP | 2009-013171 A | 1/2009 |
| JP | 2009203213 A | 9/2009 |
| JP | 2015-151370 A | 8/2015 |
| KR | 2009-0101667 A | 9/2009 |
| WO | WO 1996/019205 A1 | 6/1996 |
| WO | WO 1996/040087 A2 | 12/1996 |
| WO | WO 2003/020248 A1 | 3/2003 |
| WO | WO 2005/079779 A1 | 9/2005 |
| WO | WO 2007/129427 A1 | 11/2007 |
| WO | WO 2008/021113 A2 | 2/2008 |
| WO | WO 2010/051349 A1 | 5/2010 |
| WO | WO 2011/070361 A1 | 6/2011 |
| WO | WO 2011/081628 A1 | 7/2011 |
| WO | WO 2012/084969 A1 | 6/2012 |
| WO | WO 2012/097197 A1 | 7/2012 |
| WO | WO 2014/174564 A1 | 10/2014 |
| WO | WO 2015/053878 A1 | 4/2015 |
| WO | WO 2015/200472 A1 | 12/2015 |
| WO | WO 2016/046675 A1 | 3/2016 |
| WO | WO 2016/099198 A1 | 6/2016 |
| WO | WO 2016/209982 A1 | 12/2016 |
| WO | WO 2017/018321 A1 | 2/2017 |
| WO | WO 2017/117554 A1 | 7/2017 |
| WO | WO 2017/223402 A1 | 12/2017 |
| WO | WO 2018/022814 A1 | 2/2018 |
| WO | WO 2018/022815 A1 | 2/2018 |
| WO | WO 2018/022816 A1 | 2/2018 |
| WO | WO 2018/022817 A1 | 2/2018 |
| WO | WO 2018/022818 A1 | 2/2018 |

OTHER PUBLICATIONS

Aida et al., "Adhesive patch useful in pharmaceuticals, for delivering drugs, provides single surface of support with adhesive layer, where adhesive layer contains drug in solution stae and crystalline state", Database WPI, AN 2008-F37689 (2013).

Brantseva et al., "Rheological and adhesive properties of PIB-based pressure-sensitive adhesives with montmorillonite-type nanofillers", European Polymer Journal, vol. 76, pp. 228-244 (2016).

Chladek et al., "Steady-state bioequivalence studies of two memantine tablet and oral solution formulations in healthy volunteers", J. Appl. Biomed., vol. 6, pp. 39-45 (2008).

Choi et al., "Effect of fatty acids on the transdermal delivery of donepezil: in vitro and in vivo evaluation", Int. J. Pharm., vol. 422, No. 1-2, pp. 83-90 (2012).

Del Rio-Sancho, "Transdermal absorption of memantin—effect of chemical enhancers, iontophoresis, and role of enhancer lipophilicity", Eur J. Pharm. Biopharm., vol. 82, No. 1, pp. 164-170 (2012).

Fang et al., "Donepezil percutaneous absorption enhancer and back lining layer which includes polyethylene, polyester and ethylene-vinyl acetate copolymer", Database WPI, AN 2013-G75464 (2013).

Forchetti, "Treating patients with moderate to severe Alzheimer's disease: implications of recent pharmacologic studies", Prim. Care Companion J. Clin. Psychiatry., vol. 7, No. 4, pp. 155-161 (2005).

Fornasari et al., "Synthesis and antioxidant properties of novel memantine derivatives", Cent. Nerv. Syst. Agents Med. Chem., vol. 17, No. 2, pp. 123-128 (2017).

(56) References Cited

OTHER PUBLICATIONS

International Search Report from International Application No. PCT/US2016/038792 dated Sep. 27, 2016.
Kato, Patch used for treating Alzheimer-type dementia, comprises support portion, adhesive layer, donepezil and/or its hydrochloride, and additive chosen from isostearic acid, 2-cetyl ethylhexanoate, and hexadecyl isostearate, Database WPI, AN 2014-C88308 (2014).
Pastore et al., "Transdermal patches: history, development and pharmacology", Br. J. Pharmacol., vol. 172, No. 9, pp. 2179-2209 (2015).
Ravi and Gupta, "The treatment of alzheimers disease by using donopezil loaded transdermal patch", J. Chem. Pharm. Res., vol. 7, No. 3, pp. 806-813 (2015).
Schulz et al., "Therapeutic and toxic blood concentrations of nearly 1,000 drugs and other xenobiotics", Crit. Care, vol. 16, No. R136, 4 pgs. (2012).
Sozio et al., "Transdermal donepezil on the treatment of Alzheimer's disease", Neuropsychiatr. Dis. Treat., vol. 8, pp. 361-368 (2012).
Tiseo et al., "Pharmacokinetic and pharmacodynamic profile of donepezil HCl following evening administration", Br. J. Pharmacol., vol. 46, Suppl. 1, pp. 13-18 (1998).
Ashall, "Tobacco Facts #4: Smokers are freebasing nicotine!—The Great Tobacco Plague", Dr Frank Ashalls Blog, Retreived from the Internet: https://biochemdr1.wordpress.com/2013/11/30/tobacco-fact-4-somkers-are-freebasing-nicotine/, 7 pages (Nov. 30, 2013).
International Search Report from International Patent Application No. PCT/US2017/044047 dated Nov. 3, 2017.
Partial International Search Report from International Patent Application No. PCT/US2017/044048 dated Nov. 3, 2017.
International Search Report from International Patent Application No. PCT/US2017/044049 dated Nov. 7, 2017.
International Search Report from International Patent Application No. PCT/US2017/044050 dated Nov. 6, 2017.
International Search Report from International Patent Application No. PCT/US2017/044051 dated Nov. 2, 2017.
Cabot Corporation, "Fumed Metal Oxides". 5 pages, Retreived from the internet on May 13, 2019 from http://www.cabotcorp.com/solutions/products-plus/fumed-metl-oxides (2019).

* cited by examiner

MEMANTINE TRANSDERMAL DELIVERY SYSTEMS

CROSS-REFERENCE TO RELATED APPLICATIONS

This application claims the benefit of U.S. Provisional Application No. 62/504,391, filed May 10, 2017; U.S. Provisional Application No. 62/457,794, filed Feb. 10, 2017; U.S. Provisional Application No. 62/457,791, filed Feb. 10, 2017; U.S. Provisional Application No. 62/444,763, filed Jan. 10, 2017; U.S. Provisional Application No. 62/444,745, filed Jan. 10, 2017; U.S. Provisional Application No. 62/423,133, filed Nov. 16, 2016; and U.S. Provisional Application No. 62/367,502, filed Jul. 27, 2016, each incorporated herein by reference in its entirety.

TECHNICAL FIELD

Embodiments described herein relate to transdermal delivery systems containing memantine or a salt thereof for systemic delivery of memantine base. In other embodiments, methods for treating neurological disorders in subjects by administering the delivery systems containing the memantine compounds are described.

BACKGROUND

Memantine is an amantadine derivative with low to moderate-affinity for N-methyl-D-aspartate (NMDA) receptor. It is a noncompetitive NMDA receptor antagonist that binds preferentially to NMDA receptor-operated cation channels. It blocks the effects of excessive levels of glutamate that may lead to neuronal dysfunction. It is presently under investigation for the treatment of Alzheimer's disease. It has the chemical structure 3,5-dimethyladamantan-1-amine (Formula I):

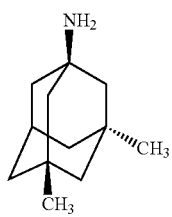

Formula I

Memantine has a molecular weight of 179.31 g/mol and is lipophilic (Log P value 3.08; reported range of 3.31-2.07; see, DRUGBANK Accession No. DB01043). It is also frequently referred to in the medical literature as 1-amino-3,5-dimethyladamantane; 1,3-dimethyl-5-adamantanamine; 3,5-dimethyl-1-adamantanamine; 3,5-dimethyl-1-aminoadamantane and 3,5-dimethyltricyclo(3.3.1.1(3,7))decan-1-amine.

An oral tablet of memantine hydrochloride (NAMENDA®; molecular weight of memantine HCl is 215.77 g/mol) is approved in the U.S. for use in treating moderate to severe Alzheimer's disease, either alone or in combination with an acetylcholinesterase inhibitor (AChEI). Due to the nature of cognitive disorders, oral medications may be subject to problems with patient compliance especially for formulations that need to be taken throughout the day.

Currently, the clinically-approved memantine hydrochloride drug is administered orally in the form of a solution or tablet. In order to allow for more convenient dosage regimen and lower pill burden with improved adherence to therapy, an extended-release (ER) formulation of memantine (NAMENDA XR®) was approved in 2010 for the treatment of Alzheimer's disease. However, the drawback of variable peak-trough fluctuation (PTF) limits administration of memantine by the oral route (Chladek et al., *J. Appl. Biomed.*, 6: 39-45, 2008). As such, transdermal administration of memantine may be an attractive alternative therapeutic option for treatment of neurological diseases such as Alzheimer's disease and vascular dementia.

To improve upon existing formulations and systems for the delivery of memantine in vivo, various strategies have been proposed, including, transdermal, injection, and rectal (suppositories) administration routes. For example, U.S. Patent Pub. No. 2008-0107719 describes a percutaneous absorption preparation of memantine for use as an anti-glaucoma drug. U.S. Patent Pub. No. 2006-0035888 describes a sustained release formulation of memantine for the treatment of schizophrenia. Other transdermal delivery systems propose using enhancers for the transdermal delivery of the drug, see e.g., U.S. Pat. No. 6,929,801. Despite these teachings, there are no memantine transdermal patches or devices available in the United States.

Transdermal patches have been approved by the FDA for the delivery of small molecules that can penetrate the skin, that are sufficiently potent to be active and that meet a clinical need (Pastore et al., *Br J Pharmacol.*, 172(9): 2179-2209, 2015). These are limited to antimuscarinic agents (e.g., scopolamine, oxybutynin), hormones (e.g., estradiol, testosterone), sodium-channel blockers (e.g., lidocaine), nitrates (e.g., nitroglycerin), adrenergic agents (e.g., clonidine), dopaminergic agents (e.g., methylphenidate), MAO inhibitors (e.g., selegiline), dopamine agonists (e.g., rotigotine) and cholinergic agents (e.g., rivastigmine). However, there is currently only one FDA-approved transdermal product for the delivery of anti-dementia drug (EXELON® rivastigmine patch manufactured by Novartis Pharmaceuticals).

Transdermal delivery of basic drugs including memantine can be especially difficult due to poor skin permeability. Further, some active agents have poor or low solubility in the adhesives and/or other components used in typical transdermal formulations. Further, there is a need for stable, long term administration of anti-dementia agents (e.g., 1-10 days or more) that provides a stable and effective release of the agent over the administration period and has suitable adhesion for the long term administration.

Therefore, there exists a need for transdermal compositions, devices and methods that address these shortcomings.

BRIEF SUMMARY

The following aspects and embodiments thereof described and illustrated below are meant to be exemplary and illustrative, not limiting in scope.

Embodiments described herein provide for compositions, systems, and methods of treating neurological diseases, such as but not limited to Alzheimer's disease. The present aspects and embodiments improve upon exiting methods by providing compositions that have been formulated for transdermal delivery of the active ingredients.

In particular, it is an object and advantage of the present compositions, systems and embodiments to confer in situ synthesis of memantine base by providing components of the synthetic machinery at the site of the application. It is contemplated that use of the in situ machinery will not only greatly improve the bioavailability of the drug, but also permit constant and sustained delivery of the drug for various therapeutic applications.

Additionally, it is contemplated that the delivery systems described herein shall provide for easy titration, optimal constant dosing, improved patience compliance, and better adherence to medication compared to the existing modes of delivery.

Embodiments described herein further relate to advantageously treating central nervous system (CNS) disorders, and in particular neurological disorders such as Alzheimer's disease, Parkinson's disease, and Huntington's disease, with the systems and devices. The instant systems and methods may help eliminate or reduce variability in absorption and high first-pass metabolism associated with orally administered memantine in patients suffering from the aforementioned neurological disorders. Additionally, the instant compositions and systems may further confer rapid and extensive drug absorption into the bloodstream without the need for hypodermic needles and injection systems. Furthermore, the ease of delivery conferred by the systems and compositions herein may increase patient adherence, while simultaneously minimizing the risk of misdosing. Finally, the systems and methods described herein may permit self-treatment by patients without the need for constant supervision from health practitioners.

In one aspect, transdermal delivery systems for systemic delivery of memantine base are provided. In embodiments, the system comprises, in series from the skin facing side, (a) a skin contact adhesive layer to attach the transdermal delivery system to the skin of a user, the skin contact adhesive layer comprised of an adhesive formulation that optionally does not comprise memantine base and/or a memantine salt; (b) optionally, an intermediate layer directly in contact with the skin contact adhesive layer; (c) a drug reservoir in contact with the intermediate layer; and (d) at least a first backing layer in contact with the drug reservoir. In embodiments, the system optionally further comprises (e) an adhesive overlay in contact with the first backing layer, and/or (f) a second backing layer in contact with the first backing layer or the adhesive overlay. In embodiments, the drug reservoir is comprised of (i) an acrylate polymer or copolymer, (ii) a dissolving agent, (iii) a carrier, (iv) an optional disintegrant, and (v) memantine base generated in situ by reaction of a salt of memantine with an alkaline salt. In some embodiments, the delivery system comprises the intermediate layer.

In embodiments, the drug reservoir layer is comprised of (i) an acrylate polymer comprising a copolymer of acrylic acid/vinyl acetate, (ii) at least one dissolving agent, (iii) at least one carrier, (iv) an optional disintegrant, and (v) memantine base generated in situ by reaction of a salt of memantine with an alkaline salt.

In another embodiment, a transdermal delivery system for systemic delivery of memantine comprises (a) a skin contact adhesive layer to attach the transdermal delivery system to the skin of a user, the skin contact adhesive layer comprising an adhesive formulation that does not comprise memantine; (b) optionally, an intermediate layer directly on the contact adhesive layer; (c) a drug reservoir layer on the intermediate layer, the drug reservoir layer comprised of (i) an acrylate polymer comprising vinyl acetate and at least one acrylate selected from the group consisting of 2-ethylhexyl-acrylate, hydroxyethyl acrylate and glycidyl acrylate, (ii) at least one dissolving agent, (iii) at least one carrier, (iv) at least one disintegrant, and (v) memantine base generated in situ by reaction of a salt of memantine with an alkaline salt; and (d) one or more additional backing layers, as detailed above.

In another embodiment, a transdermal delivery system for systemic delivery of memantine comprises (a) a skin contact adhesive layer to attach the transdermal delivery system to the skin of a user, the skin contact adhesive layer comprising an adhesive formulation that does not comprise memantine; (b) optionally, an intermediate layer directly on the contact adhesive layer; (c) a drug reservoir layer on the intermediate layer, the drug reservoir layer comprised of (i) an acrylate polymer, (ii) at least one dissolving agent which is a higher alcohol selected from the group consisting of lauryl alcohol, isostearyl alcohol, octyldodecanol, and oleyl alcohol, (iii) at least one carrier, (iv) an optional disintegrant, and (v) memantine base generated in situ by reaction of a salt of memantine with an alkaline salt; and (d) one or more additional backing layers, as detailed above.

In another embodiment, a transdermal delivery system for systemic delivery of memantine comprises (a) a skin contact adhesive layer to attach the transdermal delivery system to the skin of a user, the skin contact adhesive layer comprising an adhesive formulation that does not comprise memantine; (b) optionally, an intermediate layer directly on the contact adhesive layer; (c) a drug reservoir layer on the intermediate layer if present, the drug reservoir layer comprised of (i) an acrylate polymer, (ii) at least one dissolving agent, (iii) at least one carrier selected from the group consisting of glycerol, propylene glycol, and liquid polyethylene glycol, (iv) at least one disintegrant, and (v) memantine base generated in situ by reaction of a salt of memantine with an alkaline salt; and (d) one or more additional backing layers, as detailed above.

In another embodiment, a transdermal delivery system for systemic delivery of memantine comprises (a) a skin contact adhesive layer to attach the transdermal delivery system to the skin of a user, the skin contact adhesive layer comprising an adhesive formulation that does not comprise memantine; (b) optionally, an intermediate layer directly on the contact adhesive layer; (c) a drug reservoir layer on the intermediate layer, the drug reservoir layer comprised of (i) an acrylate polymer, (ii) at least one dissolving agent or permeation enhancer, (iii) at least one carrier that is a hydrophilic solvent, (iv) at least one disintegrant, and (v) memantine base generated in situ by reaction of a salt of memantine with an alkaline salt; and (d) one or more additional backing layers, as detailed above, wherein the skin contact adhesive layer does not comprise the hydrophilic solvent carrier.

In another embodiment, a transdermal delivery system for systemic delivery of memantine comprises (a) a skin contact adhesive layer to attach the transdermal delivery system to the skin of a user, the skin contact adhesive layer comprising an adhesive formulation that does not comprise memantine; (b) optionally, an intermediate layer directly on the contact adhesive layer; (c) a drug reservoir layer on the intermediate layer, the drug reservoir layer comprised of (i) an acrylate polymer, (ii) at least one dissolving agent, (iii) at least one carrier, (iv) at least one disintegrant selected from the group consisting of polyvinylpyrrolidone (PVP) or polyvinyl alcohol (PVA), or cross-linked derivative thereof, and (v) memantine base generated in situ by reaction of a salt of memantine with an alkaline salt; and (d) one or more additional backing layers, as detailed above. In some embodiments, the disintegrant is cross-linked polyvinylpyrrolidone.

In another embodiment, a transdermal delivery system for systemic delivery of memantine comprises (a) a skin contact adhesive layer to attach the transdermal delivery system to the skin of a user, the skin contact adhesive layer comprising an adhesive formulation that does not comprise memantine; (b) optionally, an intermediate layer directly on the contact adhesive layer, wherein the intermediate layer is a rate controlling membrane for memantine base; (c) a drug reservoir layer on the intermediate layer, the drug reservoir layer comprised of (i) an acrylate polymer, (ii) at least one dissolving agent, (iii) at least one carrier, (iv) at least one disintegrant, and (v) memantine base generated in situ by reaction of a salt of memantine with an alkaline salt; and (d) one or more additional backing layers, as detailed above. In some embodiments, the rate controlling membrane comprises microporous polypropylene. In some embodiments, the rate controlling membrane comprises non-woven polyester.

In another embodiment, a transdermal delivery system for systemic delivery of memantine comprises (a) a skin contact adhesive layer to attach the transdermal delivery system to the skin of a user, the skin contact adhesive layer comprising an adhesive formulation that does not comprise memantine; (b) optionally, an intermediate layer directly on the contact adhesive layer; (c) a drug reservoir layer on the intermediate layer, the drug reservoir layer comprised of (i) an acrylate polymer, (ii) at least one dissolving agent, (iii) at least one carrier, (iv) at least one disintegrant, and (v) memantine base generated in situ by reaction of a halide salt of memantine with an alkaline salt; and (d) one or more additional backing layers, as detailed above. In one embodiment, the halide salt comprises a chloride salt of memantine (memantine HCl).

In another embodiment, a transdermal delivery system for systemic delivery of memantine comprises (a) a skin contact adhesive layer to attach the transdermal delivery system to the skin of a user, the skin contact adhesive layer comprising an adhesive formulation that does not comprise memantine; (b) optionally, an intermediate layer directly on the contact adhesive layer; (c) a drug reservoir layer on the intermediate layer, the drug reservoir layer comprised of (i) an acrylate polymer, (ii) at least one dissolving agent, (iii) at least one carrier, (iv) at least one disintegrant, and (v) memantine base generated in situ by reaction of a salt of memantine with an alkaline salt selected from the group consisting of sodium acetate, sodium borate, sodium metaborate, sodium carbonate, sodium bicarbonate, potassium carbonate, potassium bicarbonate, potassium citrate, potassium acetate, sodium phosphate, potassium phosphate, disodium hydrogen phosphate, sodium oxylate, sodium succinate, sodium citrate, and sodium salicylate; and (d) one or more additional backing layers, as detailed above. In some embodiments, the alkaline salt comprises sodium bicarbonate or potassium bicarbonate.

In another embodiment, a transdermal delivery system for systemic delivery of memantine comprises (a) a skin contact adhesive layer to attach the transdermal delivery system to the skin of a user, the skin contact adhesive layer comprising an adhesive formulation that does not comprise memantine; (b) optionally, an intermediate layer directly on the contact adhesive layer; (c) a drug reservoir layer on the intermediate layer, the drug reservoir layer comprised of (i) an acrylate polymer, (ii) at least one dissolving agent; (iii) at least one carrier; (iv) at least one disintegrant; (v) memantine base generated in situ by reaction of a salt of memantine with an alkaline salt; and (vi) an additional agent selected from sorbitan monolaurate and lauryl lactate; and (d) one or more additional backing layers, as detailed above.

In another embodiment, a transdermal delivery system for systemic delivery of memantine comprises (a) a skin contact adhesive layer comprising a higher alcohol and a biocompatible polymer, optionally together with a matrix modifier and further optionally dispersive silica, to attach the transdermal delivery system to the skin of a user, the skin contact adhesive layer comprising an adhesive formulation that does not comprise memantine; (b) optionally, an intermediate layer directly on the contact adhesive layer; (c) a drug reservoir layer on the intermediate layer, the drug reservoir layer comprised of (i) an acrylate polymer, (ii) at least one dissolving agent; (iii) at least one carrier; (iv) an optional disintegrant; and (v) memantine base generated in situ by reaction of a salt of memantine with an alkaline salt; and (d) one or more additional backing layers, as detailed above. In some embodiments, the skin contact adhesive layer comprises a higher alcohol, a biocompatible polymer, and a matrix modifier. In another specific embodiment, the skin contact adhesive layer comprises a higher alcohol, a biocompatible polymer, and dispersive silica.

In another embodiment, a transdermal delivery system for systemic delivery of memantine base comprises (a) a skin contact adhesive layer comprising a higher alcohol selected from the group consisting of lauryl alcohol, isostearyl alcohol, octyldodecanol, and oleyl alcohol, and a biocompatible polymer, optionally together with a matrix modifier and further optionally dispersive silica, to attach the transdermal delivery system to the skin of a user, the skin contact adhesive layer comprising an adhesive formulation that does not comprise memantine; (b) optionally, an intermediate layer directly on the contact adhesive layer; (c) a drug reservoir layer on the intermediate layer, the drug reservoir layer comprised of (i) an acrylate polymer, (ii) at least one dissolving agent; (iii) at least one carrier; (iv) at least one disintegrant; and (v) memantine base generated in situ by reaction of a salt of memantine with an alkaline salt; and (d) one or more additional backing layers, as detailed above.

In another embodiment a transdermal delivery system for systemic delivery of memantine comprises (a) a skin contact adhesive layer comprising a higher alcohol and a biocompatible polymer selected from the group consisting of polyisobutylene (PIB), a silicone polymer, acrylate copolymers, butyl rubber, polybutylene, styrene-iosprene-styrene block copolymers, styrene-butadiene-styrene block copolymers, ethylene-vinyl acetate (EVA), a mixture thereof or a copolymer thereof, optionally together with a matrix modifier and further optionally dispersive silica, to attach the transdermal delivery system to the skin of a user, the skin contact adhesive layer comprising an adhesive formulation that does not comprise memantine; (b) optionally, an intermediate layer directly on the contact adhesive layer; (c) a drug reservoir layer on the intermediate layer, the drug reservoir layer comprised of (i) an acrylate polymer, (ii) at least one dissolving agent; (iii) at least one carrier; (iv) an optional disintegrant; and (v) memantine base generated in situ by reaction of a salt of memantine with an alkaline salt; and (d) one or more additional backing layers, as detailed above. In some embodiments, the biocompatible polymer comprises polyisobutylene or a blend or mixture of polyisobutylene and polybutene.

In another embodiment, a transdermal delivery system for systemic delivery of memantine comprises (a) a skin contact adhesive layer comprising a higher alcohol and a biocompatible polymer, optionally together with a matrix modifier selected from the group consisting of cross-linked polyvinylpyrrolidone (PVP), soluble PVP, cellulose derivatives, polyacrylamide, polyacrylic acid and clay, and further optionally dispersive silica, to attach the transdermal delivery system to the skin of a user, the skin contact adhesive layer comprising an adhesive formulation that does not comprise memantine; (b) optionally, an intermediate layer directly on the contact adhesive layer; (c) a drug reservoir layer on the intermediate layer, the drug reservoir layer comprised of (i) an acrylate polymer, (ii) at least one dissolving agent; (iii) at least one carrier; (iv) at least one disintegrant; and (v) memantine base generated in situ by reaction of a salt of memantine with an alkaline salt; and (d) one or more additional backing layers, as detailed above. In some embodiments, the matrix modifier is a cross-linked polyvinylpyrrolidone.

In another embodiment, a transdermal delivery system for systemic delivery of memantine comprises (a) a skin contact adhesive layer comprising a higher alcohol and a biocompatible polymer, optionally together with a matrix modifier, and further optionally pharmaceutical grade amorphous anhydrous colloidal silicon dioxide, to attach the transdermal delivery system to the skin of a user, the skin contact adhesive layer comprising an adhesive formulation that does not comprise memantine; (b) optionally, an intermediate layer directly on the contact adhesive layer; (c) a drug reservoir layer on the intermediate layer, the drug reservoir layer comprised of (i) an acrylate polymer, (ii) at least one dissolving agent; (iii) at least one carrier; (iv) at least one disintegrant; and (v) memantine base generated in situ by reaction of a salt of memantine with an alkaline salt; and (d) one or more additional backing layers, as detailed above.

In another embodiment, transdermal delivery systems for systemic delivery of memantine are provided. The delivery system comprises (a) a skin contact adhesive layer to attach the transdermal delivery system to the skin of a user, the skin contact adhesive layer comprising an adhesive formulation that does not comprise memantine; (b) optionally, an intermediate layer directly on the contact adhesive layer; (c) a drug reservoir layer on the intermediate layer, the drug reservoir layer comprised of (i) an acrylate polymer, (ii) at least one dissolving agent, (iii) at least one carrier; (iv) at least one disintegrant, and (v) memantine base generated in situ by reaction of a salt of memantine with an alkaline salt; and (d) a first backing layer in contact with the adhesive matrix drug reservoir layer; an adhesive overlay comprising polyisobutylene, polybutene or a mixture thereof in contact with the first backing layer; and a second backing layer in contact with the adhesive overlay. In one particular embodiment, the adhesive overlay is comprised of a first layer and a second layer, the first layer composed of a polyisobutylene, polybutene or a mixture thereof and the second layer composed of an acrylic adhesive. In another embodiment, the adhesive overlay is fused to the drug reservoir matrix, layered on top of the reservoir matrix, or separated from the reservoir matrix by at least one intermediate layer. In another embodiment, the adhesive overlay is a single layer comprised of an acrylate polymer or copolymer.

In a related embodiment, compositions comprising solid monolithic drug reservoir comprising (i) memantine base generated in situ by reaction of a salt of memantine with an alkaline salt; (ii) a carrier and (iii) an acrylate polymer are provided. In one embodiment, the carrier is glycerol.

In another embodiment, compositions comprising an adhesive matrix comprising (i) memantine base generated in situ by reaction of a salt of memantine with an alkaline salt; (ii) at least one carrier; (iii) an acrylate polymer; and at least one dissolving agent are provided. In some embodiments, the dissolving agent is a higher alcohol selected from the group consisting of lauryl alcohol, isostearyl alcohol, octyldodecanol, and oleyl alcohol.

In another embodiment, compositions comprising an adhesive matrix comprising (i) memantine base generated in situ by reaction of a salt of memantine with an alkaline salt; (ii) at least one carrier and (iii) an acrylate polymer, wherein adhesive matrix comprises a crosslinked polyvinylpyrrolidone are provided.

In another embodiment, an adhesive matrix comprising (i) memantine base generated in situ by reaction of memantine hydrochloride with an alkaline salt selected from the group consisting of sodium acetate, sodium borate, sodium metaborate, sodium carbonate, sodium bicarbonate, potassium carbonate, potassium bicarbonate, potassium citrate, potassium acetate, sodium phosphate, potassium phosphate, disodium hydrogen phosphate, sodium oxylate, sodium succinate, sodium citrate, and sodium salicylate; (ii) a carrier; and (iii) an acrylate polymer is provided.

In yet another embodiment, compositions comprising an adhesive matrix or polymeric solid monolith consisting essentially of a memantine base generated in situ by reaction of a salt of memantine and an alkaline salt; at least one dissolving agent; at least one carrier; and a polymeric, adhesive matrix comprising crosslinked polyvinylpyrrolidone and an acrylate polymer are provided.

In one embodiment, compositions comprising a drug reservoir consisting essentially of (a) memantine base generated in situ by reaction of between about 5-50 wt % or 10-30 wt % memantine salt and between about 5-15 wt % alkaline salt; (b) about 5-15 wt % dissolving agent; (c) about 5-15 wt % carrier; (d) about 10-30 wt % disintegrant; and (e) about 10-65 wt % or 20-65 wt % or 20-50 wt % acrylate copolymer are provided. In some embodiments, the memantine salt is memantine hydrochloride (memantine HCl); in some embodiments, the alkaline salt is sodium bicarbonate or potassium bicarbonate; in some embodiments, the dissolving agent is a higher alcohol selected from the group consisting of lauryl alcohol, isostearyl alcohol, octyldodecanol, and oleyl alcohol; in embodiments, the carrier is glycerol; in some embodiments, the disintegrant is cross-linked polyvinylpyrrolidone (PVP-CLM); in embodiments, the acrylate polymer comprises vinyl acetate and at least one acrylate selected from the group consisting of 2-ethylhexyl-acrylate, hydroxyethyl acrylate and glycidyl acrylate.

In another embodiment, compositions comprising a drug reservoir consisting essentially of (a) memantine base generated in situ by reaction of between about 22-27 wt % memantine salt and between about 7-12 wt % alkaline salt; (b) about 8-12 wt % dissolving agent; (c) about 8-12 wt % carrier; (d) about 13-17 wt % disintegrant; and (e) about 28-35 wt % acrylate polymer are provided. In embodiments, the memantine salt is memantine hydrochloride (memantine HCl); in some embodiments, the alkaline salt is sodium bicarbonate or potassium bicarbonate; in some embodiments, the dissolving agent is a higher alcohol selected from the group consisting of lauryl alcohol, isostearyl alcohol, octyldodecanol, and oleyl alcohol; in some embodiments, the carrier is glycerol; in some embodiments, the disintegrant is crosslinked polyvinylpyrrolidone (PVP-CLM); in some embodiments, the acrylate polymer comprises vinyl acetate and at least one acrylate selected from the group consisting of 2-ethylhexyl-acrylate, hydroxyethyl acrylate and glycidyl acrylate.

In another embodiment, compositions comprising (a) one or more of the aforementioned drug reservoirs; (b) a rate controlling membrane or a non-woven layer; and (c) an adhesion matrix; and (d) optionally a permeation enhancer are provided. In some embodiments, the rate controlling membrane is a microporous polypropylene membrane.

In one embodiment, the microporous membrane has a plurality of pores. The plurality of pores in the microporous membrane contain a solvent or a solvent composition. In one embodiment, the solvent composition in the pores of the microporous membrane is comprised of one or more of the solvents present in either or both of the drug reservoir and the contact adhesive, exclusive of the hydrophilic solvent or carrier in the drug reservoir.

In another embodiment, compositions comprising (a) one or more of the aforementioned drug reservoirs; (b) a rate controlling membrane or a non-woven layer; and (c) an adhesion matrix comprising a higher alcohol and a biocompatible polymer, optionally together with a matrix modifier and further optionally dispersive silica are provided. In some embodiments, the adhesion matrix comprises the higher alcohol, the biocompatible polymer and the matrix modifier. In some embodiments, the adhesion matrix comprises the higher alcohol, the biocompatible polymer and the dispersive silica. In some embodiments, the adhesion matrix does not comprise the hydrophilic solvent or carrier in the drug reservoir, and in a specific embodiment does not comprise glycerol.

In a related embodiment, compositions comprising (a) one or more of the aforementioned drug reservoirs; (b) a rate controlling membrane or a non-woven layer; and (c) an adhesion matrix comprising a higher alcohol selected from the group consisting of lauryl alcohol, isostearyl alcohol, octyldodecanol, and oleyl alcohol and a biocompatible polymer comprising polyisobutylene (PIB), silicone polymers, acrylate copolymers, butyl rubber, polybutylene, styrene-iosprene-styrene block copolymers, styrene-butadiene-styrene block copolymers, ethylene-vinyl acetate (EVA), or a mixture thereof or a copolymer thereof, optionally together with a matrix modifier selected from the group consisting of cross-linked polyvinylpyrrolidone (PVP), soluble PVP, cellulose derivatives, polyacrylamide, polyacrylic acid and clay and further optionally high purity amorphous anhydrous colloidal silicon dioxide are provided.

In one particular embodiment, compositions comprising (a) one or more of the aforementioned drug reservoirs; (b) a rate controlling membrane or a non-woven layer; and (c) an adhesion matrix comprising about 5-15 wt % of a higher alcohol and about 50-95 wt % of a biocompatible polymer, optionally together with about 10-30 wt % of a matrix modifier and further optionally about 4-12 wt % of dispersive silica are provided. In some embodiments, the adhesion matrix comprises a higher alcohol which is octyldodecanol, a biocompatible polymer comprising polyisobutylene, and optionally a matrix modifier comprising cross-linked polyvinylpyrrolidone (PVP) and further optionally dispersive silica comprising high purity amorphous anhydrous colloidal silicon dioxide.

In another particular embodiment, compositions comprising (a) one or more of the aforementioned drug reservoirs; (b) a rate controlling membrane or a non-woven layer; and (c) an adhesion matrix comprising about 8-12 wt % of a higher alcohol and about 65-90 wt % of a biocompatible polymer, optionally together with about 15-25 wt % of a matrix modifier and further optionally about 5-10 wt % of dispersive silica are provided. In some embodiments, the adhesion matrix comprises a higher alcohol which is octyldodecanol, a biocompatible polymer comprising polyisobutylene, and optionally a matrix modifier comprising cross-linked polyvinylpyrrolidone (PVP) and further optionally dispersive silica comprising high purity amorphous anhydrous colloidal silicon dioxide.

In a related embodiment, kits comprising, in one or more packages, (a) one or more of the aforementioned drug reservoirs; (b) a rate controlling membrane or a non-woven layer; and (c) an adhesion matrix, optionally together with instructions for assembling components (a)-(c) into a delivery system, and additionally or optionally together with instructions for administering the composition or the delivery system to a subject in need thereof are provided.

In an additional aspect, a kit comprising, in one or more packages, (i) a composition comprising (a) a drug reservoir comprised of an adhesive matrix comprising (i) memantine base generated in situ by reaction of a salt of memantine with an alkaline salt; (ii) a carrier, and (iii) an acrylate polymer; (b) a rate controlling membrane or a non-woven layer; and (c) an adhesion matrix, (ii) instructions for assembling the components into a delivery system, and/or (iii) instructions for administering the composition or the delivery system to a subject in need thereof.

In a further aspect, methods for delivering memantine to a subject in need thereof comprising contacting a tissue of the subject with a transdermal delivery system as described herein or a transdermal delivery system comprising a composition as described herein are provided. In a particular embodiment, the tissue is skin tissue, e.g., cutaneous skin tissue or mucous skin tissue. In embodiments, the subject is a human subject who is suffering from or has been diagnosed with a CNS disorder, e.g., Alzheimer's disease, vascular dementia or a combination thereof.

DETAILED DESCRIPTION

Figure 1A:
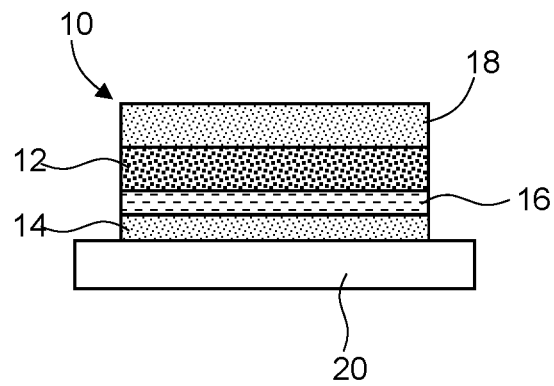
FIGS. 1A-1D are illustrations of transdermal delivery systems according to several embodiments.

Various aspects now will be described more fully hereinafter. Such aspects may, however, be embodied in many different forms and should not be construed as limited to the embodiments set forth herein; rather, these embodiments are provided so that this disclosure will be thorough and complete, and will fully convey its scope to those skilled in the art.

Throughout this disclosure, various patents, patent applications and publications are referenced. The disclosures of these patents, patent applications and publications in their entireties are incorporated into this disclosure by reference in order to more fully describe the state of the art as known to those skilled therein as of the date of this disclosure. This disclosure will govern in the instance that there is any inconsistency between the patents, patent applications and publications cited and this disclosure.

I. Definitions

Where a range of values is provided, it is intended that each intervening value between the upper and lower limit of that range and any other stated or intervening value in that stated range is encompassed within the disclosure. For example, if a range of 1 μm to 8 μm is stated, it is intended that 2 μm, 3 μm, 4 μm, 5 μm, 6 μm, and 7 μm are also explicitly disclosed, as well as the range of values greater than or equal to 1 μm and the range of values less than or equal to 8 μm.

The singular forms "a," "an," and "the" include plural referents unless the context clearly dictates otherwise. Thus, for example, reference to a "polymer" includes a single polymer as well as two or more of the same or different polymers, reference to an "excipient" includes a single excipient as well as two or more of the same or different excipients, and the like.

The word "about" when immediately preceding a numerical value means a range of plus or minus 10% of that value, e.g., "about 50" means 45 to 55, "about 25,000" means 22,500 to 27,500, etc., unless the context of the disclosure indicates otherwise, or is inconsistent with such an interpretation. For example in a list of numerical values such as "about 49, about 50, about 55, "about 50" means a range extending to less than half the interval(s) between the preceding and subsequent values, e.g., more than 49.5 to less than 52.5. Furthermore, the phrases "less than about" a value or "greater than about" a value should be understood in view of the definition of the term "about" provided herein.

"Substantially" or "essentially" means nearly totally or completely, for instance, 90-95% or greater of some given quantity. "Substantially free" means nearly totally or completely absent of some given quantity such as being present at a level of less than about 1-5% of some given quantity. In some embodiments, "substantially free" means presence at a level of less than or equal to 1-5% by weight of the pharmaceutical composition.

The terms "skin" tissue or "cutaneous" tissue as used herein are defined as including tissues covered by a stratum corneum, or stratum lucidum, and/or other mucous membranes. The term further includes mucosal tissue, including the interior surface of body cavities, e.g., buccal, nasal, rectal, vaginal, etc., which have a mucosal lining. The term "skin" should be interpreted as including "mucosal tissue" and vice versa.

The terms "transdermal" and "topical" are used herein in the broadest sense to refer to administration of a drug, e.g., a memantine compound or composition thereof, to the skin surface or mucosal membrane of an animal, including humans, so that the drug passes through the body surface, e.g., skin, and into the individual's blood stream. The term "transdermal" is intended to include trans-mucosal administration, i.e., administration of a drug to the mucosal (e.g., sublingual, buccal, vaginal, rectal) surface of an individual so that the agent passes through the mucosal tissue and into the individual's blood stream.

The terms "topical delivery system," "transdermal delivery system" and "TDS," which refer to the route of delivery of the drug via the skin tissue, are used interchangeably.

The phrase "pharmaceutically acceptable" is employed herein to refer to those compounds, salts, compositions, dosage forms, etc., which are—within the scope of sound medical judgment—suitable for use in contact with the tissues of human beings and/or other mammals without excessive toxicity, irritation, allergic response, or other problem or complication, commensurate with a reasonable benefit/risk ratio. In some aspects, "pharmaceutically acceptable" means approved by a regulatory agency of the federal or a state government, or listed in the U.S. Pharmacopeia or other generally recognized pharmacopeia for use in mammals (e.g., animals), and more particularly, in humans.

II. Transdermal Delivery System and Compositions for Use in a Transdermal Delivery System A transdermal delivery system for systemic delivery of memantine and compositions for use in a transdermal delivery system are provided. The transdermal system in general is comprised of a skin contact adhesive layer and a drug reservoir, where the two may be separated by an intermediate layer that is typically, but not always, a fabric or membrane or other non-adhesive material. The compositions and the layers of the system are now described.

In some embodiments, the drug reservoir comprises, as an active ingredient, one or more drugs. Preferably, the terms "drug" or "active agent" or "therapeutic agent" each refer to memantine compounds, including, derivatives thereof, salts thereof, hydrates or alcoholates thereof, tautomers or stereoisomers thereof, or mixtures thereof. The terms "active agent", "drug" or "therapeutically active agent" are used interchangeably herein.

The drug reservoir layer, in one embodiment, is comprised of a composition comprising, one or more adhesive polymers, memantine base generated in situ by reaction of memantine, e.g. a memantine salt, and an alkaline salt. In some embodiments, the drug reservoir layer is comprised of a composition comprising one or more adhesive polymers, at least one dissolving agent, optionally together with a permeation enhancer, at least one carrier, optionally at least one disintegrant, memantine base generated in situ by reaction of memantine, e.g. a memantine salt, and an alkaline salt. The composition may further include other components and agents such as gelling agents, emollients, surfactants, humectants, viscosity enhancers, emulsifiers, etc.

The term "drug reservoir" means a composition made to retain and release a drug for transdermal delivery, which composition is produced by combining a drug and a matrix material. The drug reservoir can be a drug reservoir composition, a solid layer, a solid adhesive layer, or a liquid layer. In some embodiments, a drug reservoir can be a drug reservoir solid layer in a multi-laminate transdermal drug delivery medical device. When combined with an adhesive, the drug reservoir can also be a solid adhesive layer, which can be used, for example, in a monolith transdermal drug delivery medical device. The drug reservoir can also comprise permeation enhancers, plasticizers, and any other suitable additive, unless otherwise noted.

In embodiments, the composition comprises as active ingredient, a memantine compound or a derivative thereof. Memantine is a compound that belongs to the admantane class of active agents. In some embodiments, the compound comprises the structure shown in Formula I above. In another embodiment, the memantine compound is also known as 3,5-dimethyladamantan-1-amine; 1-amino-3,5-dimethyladamantane; 1,3-dimethyl-5-adamantanamine; 3,5-dimethyl-1-adamantanamine; 3,5-dimethyl-1-aminoadamantane; and 3,5-dimethyltricyclo(3.3.1.1(3,7))decan-1-amine.

In another embodiment, the compositions comprise derivatives of the aforementioned memantine compounds. The term "derivative" as used herein includes salts, amides, esters, enol ethers, enol esters, acetals, ketals, orthoesters, hemiacetals, hemiketals, acids, bases, solvates, hydrates or prodrugs of the aforementioned compounds. Such derivatives may be readily prepared by those of skill in this art using known methods for such derivatization. In certain embodiments, the derivatives may be administered to animals or humans without substantial toxic effects and either are pharmaceutically active or are prodrugs. Representative types of memantine derivatives are described in U.S. Pat. Nos. 3,391,142; 4,122,193; 4,273,774; and 5,061,703; U.S. Pat. Pub. Nos. 2004-0087658; 2005-0113458; 2006-0205822; 2009-0081259; 2009-0124659; and 2010-0227852; Eur. Pat. Pub. Nos. EP2260839A2; EP1682109B1; and Int. Pat. Pub. No. WO2005079779. For instance, antioxidant memantine derivatives containing N-acetyl-Cys-OH and N-acetyl-Cys(Allyl)-OH are described in Cacciatore et al., *Cent Nerv Syst Agents Med Chem.*, 2016 (PMID: 27356627).

In another embodiment, the compositions comprise salts of the aforementioned memantine compounds. The term "salt" includes salts derived from a variety of organic and inorganic counter ions well known in the art and include, by way of example, a hydrochloric acid salt, a hydrobromic acid salt, a sulfuric acid salt, a phosphoric acid salt, a metaphosphoric acid salt, an acetic acid salt, a propionic acid salt, a hexanoic acid salt, a cyclopentanepropionic acid salt, a glycolic acid salt, a pyruvic acid salt, a lactic acid salt, a malonic acid salt, a succinic acid salt, a malic acid salt, a L-malic acid salt, a maleic acid salt, an oxalic acid salt, a fumaric acid salt, a trifluoroacetic acid salt, a tartaric acid salt, a L-tartaric acid salt, a citric acid salt, a benzoic acid salt, a 3-(4-hydroxybenzoyl)benzoic acid salt, a cinnamic acid salt, a mandelic acid salt, a methanesulfonic acid salt, an ethanesulfonic acid salt, a 1,2-ethanedisulfonic acid salt, a 2-hydroxyethanesulfonic acid salt, a benzenesulfonic acid salt, a toluenesulfonic acid salt, a 2-naphthalenesulfonic acid salt, a 4-methylbicyclo-[2.2.2]oct-2-ene-1-carboxylic acid salt, a glucoheptonic acid salt, a 4,4'-methylenebis-(3-hydroxy-2-ene-1-carboxylic acid) salt, a 3-phenylpropionic acid salt, a trimethylacetic acid salt, a tertiary butylacetic acid salt, a lauryl sulfuric acid salt, a gluconic acid salt, a glutamic acid salt, a hydroxynaphthoic acid salt, a salicylic acid salt, a stearic acid salt, a muconic acid salt, a butyric acid salt, a phenylacetic acid salt, a phenylbutyric acid salt, or a valproic acid salt. In some embodiments, the salt of the compound is a hydrochloric acid salt.

In embodiments, the memantine compound is a memantine halide salt (e.g., chloride, bromide, iodide), especially a hydrochloride salt of memantine.

In some embodiments, the salt of the compound is formed by reacting the compound with an inorganic acid. In some embodiments, the salt of the compound is formed by reacting the compound with an inorganic acid, wherein the inorganic acid is hydrochloric acid, hydrobromic acid, sulfuric acid, phosphoric acid, or metaphosphoric acid. In some embodiments, the salt of the compound is formed by reacting the compound with an organic acid. In some embodiments, the salt of the compound is formed by reacting the compound with an organic acid, wherein the organic acid is acetic acid, propionic acid, hexanoic acid, cyclopentanepropionic acid, glycolic acid, pyruvic acid, lactic acid, malonic acid, succinic acid, malic acid, L-malic acid, maleic acid, oxalic acid, fumaric acid, trifluoroacetic acid, tartaric acid, L-tartaric acid, citric acid, benzoic acid, 3-(4-hydroxybenzoyl)benzoic acid, cinnamic acid, mandelic acid, methanesulfonic acid, ethanesulfonic acid, 1,2-ethanedisulfonic acid, 2-hydroxyethanesulfonic acid, benzenesulfonic acid, toluenesulfonic acid, 2-naphthalenesulfonic acid, 4-methylbicyclo-[2.2.2]oct-2-ene-1-carboxylic acid, glucoheptonic acid, 4,4'-methylenebis-(3-hydroxy-2-ene-1-carboxylic acid), 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, butyric acid, phenylacetic acid, phenylbutyric acid, or valproic acid.

In some embodiments, described herein is a hydrochloride salt of a compound that has the structure of Formula (I). In a particular embodiment, the memantine salt includes memantine hydrochloride.

In another embodiment, the compositions comprise solvent addition forms of the aforementioned memantine compounds, e.g., solvates and alcoholates. Solvates contain either stoichiometric or non-stoichiometric amounts of a solvent, and may be formed during the process of crystallization with acceptable solvents such as water, ethanol, and the like. Hydrates are formed when the solvent is water; alcoholates are formed when the solvent is alcohol. Solvates of compounds described herein can be conveniently prepared or formed using routine techniques. In one embodiment, the solvates comprise complexes of the memantine compound with one or more solvent (e.g., water or alcohol) molecules, or 1 to about 100, or 1 to about 10, or one to about 2, 3 or 4, solvent molecules per molecule of the memantine compound. In other embodiments, the compounds provided herein can exist in unsolvated as well as solvated forms.

In another embodiment, the compositions comprise amides or esters of the aforementioned memantine compounds. The term "amide" refers to refers to either —N($R^1$)—C(=O)— or —C(=O)—N($R^1$)— wherein $R^1$ is defined herein to include hydrogen as well as other groups. The term "substituted amide" refers to the situation where R1 is not hydrogen, while the term "unsubstituted amide" refers to the situation where R1 is hydrogen. In one embodiment, the amide group is unsubstituted or substituted via the nitrogen atom by alkyl ($C_1$-$C_8$) group, aryl ($C_1$-$C_8$) group, phenyl, carbocyclic ($C_3$-$C_8$) group, heterocyclic ($C_3$-$C_8$) group, acyl, alkyl ($C_1$-$C_8$) halide, or alkenyl ($C_1$-$C_8$) group. The term "ester" refers to a chemical compound derived from an acid (organic or inorganic) in which at least one hydroxyl group is replaced by an alkoxy group. Representative types of "esters" include, but are not limited to, alkyl, alkenyl, alkynyl, aryl, heteroaryl, aralkyl, heteroaralkyl, cycloalkyl and heterocyclyl esters of acidic groups, including, but not limited to, carboxylic acids, phosphoric acids, phosphinic acids, sulfonic acids, sulfinic acids and boronic acids.

In another embodiment, the compositions comprise isomers of the aforementioned memantine compounds. The term "isomer" includes compounds with the same formula but a different arrangement of atoms in the molecule. Preferably, the isomers of the memantine compounds are "tautomers" or "stereoisomers" of the compounds of Formula I. The term "stereoisomer" refers to compounds that differ in the chirality of one or more stereocenters. Stereoisomers include enantiomers and diastereomers. The term "tautomer" refers to alternate forms of a compound that differ in the position of a proton, such as enol-keto and imine-enamine tautomers, or the tautomeric forms of heteroaryl groups containing a ring atom attached to both a ring —NH— moiety and a ring =N— moiety such as pyrazoles, imidazoles, benzimidazoles, triazoles, and tetrazoles. Preferably, the tautomers and the steroisomers of the compounds of Formula I have similar or same biological properties, e.g., with respect to NMDA receptor antagonism, as the parent compounds.

In some embodiments, the compositions comprise prodrugs of the aforementioned memantine compounds. The term "prodrug" refers to any derivative of a compound of the embodiments that is capable of directly or indirectly providing a compound of the embodiments or an active metabolite or residue thereof when administered to a subject. Particularly favored derivatives and prodrugs are those that increase the bioavailability of the compounds of the embodiments when such compounds are administered to a subject (e.g., by allowing a transdermally-administered compound to be more readily absorbed into the skin tissue) or which enhance delivery of the parent compound to a biological compartment (e.g., the brain) relative to the parent species.

Prodrugs include amide and ester forms of the compounds. Examples of ester prodrugs include formate, acetate, propionate, butyrate, acrylate, and ethylsuccinate derivatives. A general overview of prodrugs is provided in Higuchi et al., *Pro drugs as Novel Delivery Systems*, Vol. 14 of the American Chemical Society Symposium Series and Edward B. Roche, ed., *Bioreversible Carriers in Drug Design*, American Pharmaceutical Association and Pergamon Press, 1987, both of which are incorporated herein by reference.

In some embodiments, the compounds include mixtures of the aforementioned memantine compounds. The term "mixture" refers to a mingling together of two or more substances without the occurrence of a reaction by which they would lose their individual properties. For instance, a mixture of compound A and compound B may contain any weight ratio of compound A and compound B, such that the total weight of the mixture would amount to 100%, e.g., 99:1 weight ratio of compound A/compound B or 1:99 weight ratio of compound A/compound B. A typical mixture may contain about 2, 3, 4, 5, or more of the aforementioned memantine compounds.

In one embodiment, the active ingredient containing memantine is in micronized form. The term "micronized" refers to extremely fine particles that are a few microns in diameter. Methods for micronizing compounds are known in the art, e.g., jet milling pulverizing techniques disclosed in published PCT Application No. WO2011/070361. In one embodiment, the mean particle size of micronized memantine HCl used in the compositions and the systems is less than about 20 µm, less than about 5 µm, or less than about 1 µm, e.g., about 0.5 µm or even about 0.1 µm.

In one embodiment, the active ingredient of the memantine compound is in the ammonium ion form. Although the ionic form is more soluble in water (and blood) its passage through membranes is somewhat slower. Memantine in the free base form (free amine) is lipophilic and is absorbed more readily through the skin cells and penetrates the dermal barrier faster than the salt form (hydrophilic). In some embodiments of the systems, the conversion of the salt form of the drug into the free base form is accomplished in situ by providing the components, e.g., the bicarbonate and the memantine HCl together or in close proximity to each other. Optionally, a lipophilic solvent may be included to dissolve the more hydrophobic free base form of the drug. The other component(s) of the in situ synthetic process, e.g., polar or amphipathic medium for carrying out the reaction, may be included in the composition or may be provided externally.

The terms "compound" and "compounds" as used herein refers to a compound encompassed by the generic formulae disclosed herein, any subgenus of those generic formulae, and any specific compounds within the generic and subgeneric formulae. Particularly, "memantine" as used herein refers memantine as a free base as well as to memantine salts including the hydrochloride salt of 3,5-dimethyladamantan-1-amine.

In one embodiment, the transdermal delivery system comprises memantine in the form of the free base, e.g., a compound whose empirical formula as a free base is $C_{12}H_{21}N$ (having a pKa of about 10.7). The term "free base" or "freebase" refers to the conjugate base (deprotonated) form of an amine, as opposed to its conjugate acid (protonated) form. The amine may be a primary amine (e.g., $RNH_2$, wherein R is an alkyl group), secondary amine (e.g., $R^1R^2NH$, wherein $R^1$ and $R^2$ are each, individually, the same or different alkyl groups) or tertiary amine (e.g., $R^1R^2R^3N$, wherein $R^1$, $R^2$ and $R^3$ are each, individually, the same or different alkyl groups).

In certain embodiments, the amine salt is converted into the base form in situ via a decomposition reaction. As used herein, the term "in situ" refers to processes, events, objects, or components that are present or take place within the context of the system or device, including, the surrounding environment, for example, the biological material with which the device is in contact. As an example, an in situ reaction may refer to the reaction of the various components present in the device (e.g., memantine salt and an alkaline salt such as a bicarbonate), including, components provided by the human skin tissue (e.g., water, which allows the components to react in aqueous form by dissolving the memantine salt and an alkaline salt such as a bicarbonate). The term is contrasted with ex situ, which refers to outside of the environment.

In embodiments, the decomposition reaction comprises reaction with an alkaline salt, which is included in the drug reservoir layer. An "alkaline salt" or "basic salt" as used herein refers to a salt, that when dissolved in water, yields a solution with pH greater than 7.0. In some embodiments, the basic or alkaline salt is an inorganic salt of a weak acid, e.g., an alkali metal salt of a weak acid selected from the group consisting of sodium acetate, sodium borate, sodium metaborate, sodium carbonate, sodium bicarbonate, sodium phosphate, potassium carbonate, potassium bicarbonate, potassium citrate, potassium acetate, and potassium phosphate disodium hydrogen phosphate, sodium oxylate, sodium succinate, sodium citrate, and sodium salicylate. In some embodiments, the alkaline salt is sodium bicarbonate or potassium bicarbonate. In particular embodiments, the alkaline salt is one whose conjugate base from the weak acid hydrolyzes to form a basic solution. For example, with sodium carbonate ($Na_2CO_3$), the carbonate (conjugate base) from the carbonic acid (weak acid) hydrolyzes in water or other polar medium to form a basic solution. Representative examples of such alkaline salts include salts of $Li^+$, $Na^+$, $K^+$, $Rb^+$, $Mg^{2+}$, $Ca^{2+}$, $Sr^{2+}$, or $Ba^{2+}$, preferably $Na^+$, $K^+$, $Mg^{2+}$, $Ca^{2+}$, wherein the conjugate bases are, for e.g., sulfate ($SO_4^-$), nitrate ($NO_3^-$), dihydrogen phosphate ($H_2PO_4^-$), acetate ($CH_3COO^-$), oxalate, citrate, tartrate, hydrogen carbonate ($HCO_3^-$), carbonate ($CO_3^{2-}$), phosphate ($PO_4^{3-}$), hydrogen phosphate ($HPO_4^{2-}$), and hydrogen sulfide ($HS^-$). In some embodiments, the alkaline/basic salt is a bicarbonate salt of an alkali metal or an alkali earth metal, especially $Na^+$ or $K^+$.

In embodiments, the salt is selected from an acetate, oxalate, citrate, tartrate, bicarbonate, or hydrogen sulfide salt of $Na^+$, $K^+$, $Mg^{2+}$, or $Ca^{2+}$, for e.g., $Na^+HCO_3^-$, $K^+HCO_3^-$, $Mg^{2+}(HCO_3^-)_2$ or $Na^+CH_3COO^-$, etc.

In some embodiments, the alkaline salt is a bicarbonate salt. Representative bicarbonate salts include, for example, sodium bicarbonate, potassium bicarbonate, ammonium bicarbonate, or a mixture thereof. Preferably, the bicarbonate salt is sodium bicarbonate.

Purely as a representative example, wherein the salt is a bicarbonate salt, it undergoes in situ reaction with memantine HCl salt to release water, $CO_2$ and the free amine in the following manner:

$Me^x(HCO_3)_x + x*(R-NH_3^+Cl^-) \rightarrow Me^xCl_x + xH_2O + xCO_2 + xR-NH_2$, wherein Me is a metal (e.g., $Li^+$, $Na^+$, $K^+$, $Rb^+$, $Mg^{2+}$, $Ca^{2+}$, $Sr^{2+}$, or $Ba^{2+}$), x is the valency of the metal (e.g., from 1 to 3), R is the adamantane ring of memantine and $-NH_2$ is the amine group of memantine.

In one embodiment, the reaction takes place in a polar medium. In another embodiment, the reaction takes place in an amphipathic medium.

In another embodiment, memantine free base may be generated using other art-known techniques. For example, in one embodiment, the free base is generated from the salt using ion exchangers. Preferred anion exchange resins are commercially available resins containing basic (cationic) groups such as quaternary ammonium groups, tertiary sulphonium groups, quaternary phosphonium groups or alkyl pyridinium groups. Particularly preferred anion exchange resins are those containing quaternary amines, such as REXYN™ 201 (Fisher Scientific Co.), AMBERLITE™ IR A-400, (Mallinckrodt Chemical Works), IONAC™ A-540 (Matheson, Coleman and Bell), DOWEX™ I and 21K (Dow Chemical Co.), and DUOLITE™ A-101D and ES-109 (Diamond Shamrock Chemical Co.).

In certain embodiments, the memantine compound and the alkaline salt, optionally together with any other ingredients or adjuvants, may be co-micronized together into a formulation. Methods for co-micronizing ingredients are known in the art. See, e.g., U.S. Pat. No. 5,424,077, which discloses a method of co-micronizing sorbitol, glycerol and potassium bicarbonate (0.05-0.5 µm particle size range) by an air jet mill procedure.

In some embodiments, the drug reservoir comprises at least about 1-50 wt %, 5-50 wt % or 5-35 wt % of a memantine compound relative to the weight of the adhesive matrix drug reservoir (inclusive of sub-ranges). In embodiments, the adhesive matrix drug reservoir comprises at least about 5-30%, at least about 5-25%, at least about 5-20%, at least about 5-15%, at least about 5-10%, at least about 10-35%, at least about 10-30%, at least about 10-25%, at least about 10-20%, at least about 10-15%, at least about 20-35%, at least about 20-30%, at least about 20-25%, at least about 25-30% or at least about 30-35% of a memantine compound (all percentages in wt %). In one embodiment, the drug reservoir comprises at least about 22-27 wt % of a memantine compound. In some embodiments, the drug reservoir comprises at least about 0.1% wt %, including, at least 0.5%, at least 1%, at least 2%, at least 5%, at least 10%, at least 15%, at least 16%, at least 17%, at least 18%, at least 19%, at least 20%, at least 21%, at least 22%, at least 23%, at least 24%, at least 25%, at least 26%, at least 27%, at least 28%, at least 29%, at least 30%, at least 31%, at least 32%, at least 33%, at least 34%, at least 35%, at least 36%, at least 37%, at least 38%, at least 39%, at least 40% or greater % by weight of the memantine compound, wherein all values are relative to the weight of the entire reservoir.

In some embodiments, the drug reservoir composition comprises at least about 1-20 wt % of one or more alkaline salts relative to the weight of the adhesive matrix drug reservoir (inclusive of sub-ranges). In embodiments, the drug reservoir comprises at least about 1-15%, at least about 1-10%, at least about 1-5%, at least about 5-20%, at least about 5-15%, at least about 5-10%, at least about 10-20%, at least about 10-15%, or at least about 15-20% at least one alkaline salt (all percentages in wt %). In some embodiments, the adhesive matrix drug reservoir composition comprises at least about 0.1% by weight relative to the weight of the entire reservoir, including, at least 0.5%, at least 1%, at least 2%, at least 3%, at least 4%, at least 5%, at least 6%, at least 7%, at least 8%, at least 9%, at least 10%, at least 11%, at least 12%, at least 13%, at least 14%, at least 15%, at least 16%, at least 17%, at least 18%, at least 19%, at least 20%, at least 25%, or greater % by weight of the one or more alkaline salts.

The adhesive component in the drug reservoir may be any of a variety of adhesive materials, such as pressure sensitive adhesive polymers. Polyacrylate pressure sensitive adhesive polymers are an example, and typically comprise a polyacrylate that is a polymer or a copolymer of a monomer or monomers selected from acrylic acid esters and methacrylic acid esters. Other monomers, such as acrylic acid and vinyl acetate, may be present. In embodiments, the acrylic polymer is based on acrylic esters such as 2-ethylhexyl acrylate (2-EHA) and ethyl acrylate. In some embodiments, the polyacrylate polymer is a polymer or a copolymer of a monomer or monomers selected from acrylic acid and vinyl acetate. In embodiments, the acrylic polymer adhesive has pendent carboxyl (—COOH) or hydroxyl (—OH) functional groups. In embodiments, the acrylic polymer adhesive comprises at least one of polyacrylate, polymethacrylate, derivatives thereof, and co-polymers thereof. In embodiments, the acrylic adhesive is comprised of an acrylate copolymer comprising acrylic ester monomers, acrylic acid, and/or vinyl acetate monomers. A copolymer of acrylic acid and vinyl acetate is one example. Acrylate copolymers are sold under the trade-name DURO-TAK® and include, but are not limited to, DURO-TAK 387-2516, 387-2051, 387-2074, and 387-2287 (having a monomer composition vinyl acetate, 2-ethylhexyl-acrylate, hydroxyethyl acrylate and glycidyl acrylate, see PCT Publication No. WO 96/40087). In embodiments, the adhesive polymer is an acrylate polymer or copolymer, e.g., a copolymer of acrylic acid/vinyl acetate selected such as hydroxyl group-containing polyacrylates, and including cross-linked derivatives thereof.

The drug reservoir may also comprise a polyvinylpyrrolidone (PVP). PVP is a water-soluble polymer comprised of the N-vinylpyrrolidone monomer, and is available in various forms, including cross-linked and non-crosslinked. In some of the working examples herein, a cross-linked PVP is included in the adhesive matrix drug reservoir such as the crosslinked polyvinylpyrrolidone sold as KOLLIDON and including KOLLIDON CL-M.

In some embodiments, the drug reservoir comprises at least about 20-80 wt % of adhesive polymers relative to the weight of the adhesive matrix drug reservoir (inclusive of sub-ranges). In embodiments, the adhesive matrix drug reservoir comprises at least about 35-80%, 30-75%, at least about 40-75%, at least about 50-75%, at least about 60-75%, at least about 25-70%, at least about 30-70%, at least about 40-70%, at least about 50-70%, at least about 60-70%, at least about 25-60%, at least about 30-60%, at least about 40-60%, at least about 50-60%, at least about 20-50%, at least about 25-50%, at least about 30-50%, at least about 35-50%, at least about 40-50%, at least about 20-45%, at least about 25-45%, at least about 30-45%, at least about 40-45%, at least about 50-45%, at least about 20-40%, at least about 25-40%, at least about 30-40%, at least about 35-40%, at least about 20-35%, at least about 25-35%, at least about 30-35%, at least about 25-30%, at least about 20-30%, at least about 20-25% of an adhesive polymer or copolymer or mixture of polymers and/or copolymers (all percentages in wt %). In embodiments, the drug reservoir comprises at least about 8%, about 10%, about 12%, about 14%, about 16%, about 18%, about 20%, about 21%, about 22%, about 23%, about 24%, about 25%, about 26%, about 27%, about 28%, about 29%, about 30%, about 31%, about 32%, about 33%, about 34%, about 35%, about 36%, about 37%, about 38%, about 39%, about 40%, about 45%, about 50%, or greater of an adhesive polymer or copolymer or mixture of polymers and/or copolymers (all percentages in wt %). It will be appreciated that the drug reservoir adhesive matrix may include one or more or at least one adhesive polymers or copolymers. In embodiments, the adhesive matrix drug reservoir comprises at least about 5-75% of an individual polymer relative to the total weight of the polymers in the matrix. In embodiments, the adhesive matrix drug reservoir comprises at least about 5-10%, 5-15%, 5-20%, 5-25%, 5-30%, 5-40%, 5-50%, 5-60%, 5-70%, 5-75%, 10-15%, 10-20%, 10-20%, 10-25%, 10-30%, 10-40%, 10-50%, 10-60%, 10-70%, 10-75%, 15-20%, 15-25%, 15-30%, 15-40%, 15-50%, 15-60%, 15-70%, 15-75%, 20-25%, 20-30%, 20-40%, 20-50%, 20-60%, 20-70%, 20-75%, 25-30%, 25-40%, 25-50%, 25-60%, 25-70%, 25-75%, 30-40%, 30-50%, 30-60%, 30-70%, 30-75%, 40-50%, 40-60%, 40-70%, 40-75%, 50-60%, 50-70%, 50-75%, 60-70%, 60-75%, or 70-75% of an individual polymer. In one embodiment, the adhesive matrix drug reservoir comprises about 28-35 wt % or about 13-17 wt % of an individual adhesive polymer or copolymer or mixture of copolymers.

In some embodiments, the compositions of the drug reservoir layer additionally comprise at least one carrier. As used herein, the term "carrier" includes solutions, emulsions, suspensions, gels, sols, colloids, and solids, designed for delivery of the aforementioned memantine compounds to the tissue, e.g., blood tissue, skin tissue, fat tissue, nerve tissue, etc. The term "solution" refers to a liquid mixture in which the minor component (e.g., memantine compound) is uniformly distributed within the major component (e.g., buffer). "Emulsions" refer to a fine dispersion of minute droplets of one liquid in another in which it is not soluble or miscible (e.g., oil and water). "Suspensions" refer to heterogeneous mixtures in which the solute particles do not dissolve but get suspended throughout the bulk of the medium. "Gels" refer to solid jelly-like material that can have properties ranging from soft and weak to hard and tough and are defined as a substantially dilute cross-linked system, which exhibits no flow. "Sols" refer to colloidal suspensions of very small solid particles in a continuous liquid medium. The term "colloid" may be used interchangeably with the terms "gel," "sol," and "suspension" and refers to homogeneous mixtures of ultramicroscopic particles of one substance dispersed through a second substance.

In some embodiments, the carrier is a liquid. In some embodiments, the carrier is hydrophilic solvent. The liquid carrier may include an excipient suitable for application to the skin or the mucous membrane. Suitable carriers and/or excipients include aqueous or non-aqueous diluents or combination thereof. Examples of aqueous carriers and/or excipients include, but are not limited to, saline, water, dextrose or combinations thereof. Non-aqueous carriers and/or excipients include, but are not limited to, alcohols, particularly polyhydroxy alcohols such as propylene glycol, polyethylene glycol, glycerol, and vegetable and mineral oils. These aqueous and/or non-aqueous carriers and/or excipients can be added in various concentrations and combinations to form solutions, suspensions, oil-in-water emulsions or water-in-oil emulsions. In certain embodiments, the carrier and/or excipient is a polar solvent material selected from the group consisting of $C_3$-$C_4$ diols, $C_3$-$C_6$ triols, and mixtures thereof, and/or a polar lipid material selected from the group consisting of fatty alcohol esters, fatty acid esters. A mixture of the polar solvent material and the lipid material, for example, in a weight ratio of solvent material to the lipid material of about 60:40 to about 99:1, may also be used. Other suitable carriers are provided in U.S. Pat. No. 5,026,556 (Drust et al.).

In one embodiment, the carrier is a composition comprising two or more alcohols. Under this embodiment, the carrier may comprise, e.g., a mixture of octydodecanol and glycerol, wherein the weight ratio of octydodecanol and glycerol is between 2:1 to 1:2, particularly between 3:2 to 2:3, especially between 10:7 to 7:10, for e.g., 1:1. Throughout this specification, unless the context requires otherwise, the words "comprise", "comprises" and "comprising" will be understood to imply the inclusion of a stated step or element or group of steps or elements but not the exclusion of any other step or element or group of steps or elements. Thus, where the carrier comprises octydodecanol and glycerol, the composition may include other elements, e.g., buffers, surfactants, emollients and the like.

In some embodiments, the carrier is a glycol, especially, one selected from glycerol, propylene glycol, and liquid polyethylene glycol. In another embodiment, the carrier is a mixture comprising glycerol. The mixture can be comprised of glycerol and any hydrophilic solvent, including water.

In some embodiments, the drug reservoir comprises at least about 5-20 wt % of one or more carriers relative to the weight of the drug reservoir (inclusive of sub-ranges). In embodiments, the drug reservoir comprises at least about 5-15%, at least about 5-10%, at least about 8-12%, at least about 10-20%, at least about 10-15%, or at least about 15-20% of one or more carriers (all percentages in wt %). In some embodiments, the drug reservoir composition comprises at least about 0.1% by weight relative to the weight of the entire reservoir, including, at least 0.5%, at least 1%, at least 2%, at least 3%, at least 4%, at least 5%, at least 6%, at least 7%, at least 8%, at least 9%, at least 10%, at least 11%, at least 12%, at least 13%, at least 14%, at least 15%, at least 16%, at least 17%, at least 18%, at least 19%, at least 20%, at least 25% of the one or more carriers, where all values are relative to the weight of the entire reservoir layer. In other embodiments, the drug reservoir comprises between 0.1-50 wt %, 0.1-25 wt %, 0.5-25 wt %, 1-50 wt %, 1-25 wt %, 2-25 wt %, 5-25 st %, 5-20 wt %, or 5-15 wt % of the carrier.

In another embodiment, the carrier consists essentially of two or more alcohols. In yet another embodiment, the carrier consists of two alcohols.

In some embodiments, the compositions of either or both of the skin contact adhesive layer and the drug reservoir layer further one or more components which facilitate permeation of memantine across epithelial layers. Such components can be included in combination with agents that increase local pH (e.g., alkalizing agents and/or buffers). The fluidity of the composition can be maintained, for example, by the use of a coating such as lecithin, by the maintenance of the required particle size in the case of dispersion and by the use of surfactants. In many cases, isotonic agents, for example, sugars, polyalcohols such as mannitol, sorbitol, and/or sodium chloride may be included in the composition.

In certain embodiments, the drug reservoir and/or skin contact adhesive also include a component to enhance permeation of the active agent across the dermis. Suitable permeation enhancers for use in the compositions also include chitosan which increases mucosal transcellular and/or paracellular permeability independent of pKa and log P, thereby facilitating immediate local absorption. Other suitable permeation enhancers include resorcinol, surfactants, polyethylene glycol or bioacids such as citric acid, lactic acid, etc. Alternatively, microencapsulation of memantine with liposomes, polysaccharides could also be used to limit enzymatic degradation as well as enhance permeability. Other permeation enhancers suitable for use herein include peptide transport agents such as those disclosed in U.S. Pat. No. 7,176,185. In addition, suitable permeation enhancers may include, but are not limited to, dimethylsulfoxide (DMSO), dimethyl formamide (DMF), N,N-dimethylacetamide (DMA), decylmethylsulfoxide (CIOMSO), polyethylene glycol monolaurate, glycerol monolaurate, lecithin, 1-substituted azacycloheptan-2-ones such as 1-n-dodecylcyclazacycloheptan-2-one (AZONE®, Nelson Research & Development Co., Irvine, Calif.), lower alkanols (e.g., ethanol), SEPA® (available from MACROCHEM Co., Lexington, Mass.), cholic acid, taurocholic acid, bile salt type enhancers, and surfactants such as TERGITOL®, NONOXYNOL-9® and TWEEN-80®. In a particular embodiment, the permeation enhancer is menthol (typically the naturally occurring stereoisomer 1R,2S,5R-menthol, although any other stereoisomers can be used).

In certain embodiments wherein the systems and devices are deployed in the mucosa, e.g., oral mucosa, vaginal mucosa, rectal mucosa and the like, art-known permeation (or penetration) enhancers may be used, such as, for example, those disclosed in U.S. Pat. No. 7,682,628. Suitable penetration enhancers include, without limitation, polyoxyethylene 23-lauryl ether, aprotin, azone, benzalkonium chloride, cetylpyridinium chloride, cetyltrimethylammonium bromide, cyclodextrin, dextran sulfate, lauric acid, propylene glycol, lysophosphatidylcholine, menthol, methoxysalicylate, methyloleate, oleic acid, phosphatidylcholine, polyoxyethylene, polysorbate, sodium ethylenediaminetetraacetic acid (EDTA), sodium deoxycholate, sodium glycocholate, sodium glycodeoxycholate, sodium lauryl sulfate, sodium salicylate, sodium taurocholate, sodium taurodeoxycholate, sulfoxides and glycosides, and combinations thereof.

In embodiments, the penetrating or permeating enhancer is included in an amount between about 1-15%, about 1-10%, about 1-5%, about 5-15%, about 5-10%, about 2-15%, about 2-10% or about 2-5% relative to the weight of the adhesive matrix (inclusive of sub-ranges).

In certain embodiments, the carrier or other component in the drug reservoir may be buffered. In one embodiment, the drug reservoir is buffered with alkaline buffers, e.g., ammonium buffer. In another embodiment, the carriers are buffered with acidic buffers, e.g., ethanoates, citrates, lactates, acetates, etc. In another embodiment, the buffered carriers contain zwitterionic buffers, such as, glycine, alanine, valine, leucine, isoleucine and phenylalanine, TRIS, MES, ADA, ACES, PIPES, MOPSO, cholamine chloride, MOPS, BES, TES, HEPES, DIPSO, MOBS, TAPSO, acetamidoglycine, TEA, POPSO, HEPPSO, EPS, HEPPS, Tricine, TRIZMA, Glycinamide, Glycyl-glycine, HEPBS, Bicine, TAPS, AMPB, CHES, AMP, AMPSO, CAPSO, CAPS, and CABS. Buffers designated GRAS (Generally Recognized as Safe) are particularly preferred. Methods of formulating buffered compositions, e.g., via use of a properly calibrated pH probe, are known in the art.

In some embodiments, the drug reservoir composition further comprises one or more dissolving agents or permeation enhancers. Examples of the dissolving agent may include a higher fatty acid ester (isopropyl palmitate, oleyl oleate, etc.), a higher alcohol (lauryl alcohol, isostearyl alcohol, octyldodecanol, oleyl alcohol, etc.), a fatty acid (isostearic acid, lauric acid, adipic acid, sebacic acid, myristic acid, etc.), a dibasic acid diester (diethyl sebacate, diisopropyl sebacate, diisopropyl adipate, etc.), triacetin, benzyl alcohol, cetyl lactate, octyldodecyl lactate, liquid paraffin, and a mixture of two or more kinds thereof.

In some embodiments, the dissolving agent or permeation enhancer is a higher alcohol, e.g., a $C_{10-30}$ alcohol that is particularly a monovalent saturated or unsaturated aliphatic alcohol, wherein the hydrocarbyl group moiety is a straight chain or branched in some embodiments. In some embodiments the higher alcohol has a melting point of at least 40° C. The $C_{10-30}$ higher alcohol used herein includes, e.g., lauryl alcohol, myristyl alcohol, palmityl alcohol, stearyl alcohol, behenyl alcohol, hexadecyl alcohol, oleyl alcohol, isostearyl alcohol, hexyldodecanol, octyldodecanol, cetostearyl alcohol, 2-decyltetradecynol, cholesterol, sitosterol, phytosterol, lanosterol, lanolin alcohol, hydrogenated lanolin alcohol, and so forth. In particular embodiments, a higher alcohol is selected from lauryl alcohol, isostearyl alcohol, octyldodecanol and oleyl alcohol.

In some embodiments, the drug reservoir comprises at least about 2-20 wt % of one or more dissolving agents or permeation enhancer relative to the weight of the drug reservoir (inclusive of sub-ranges). In embodiments, the drug reservoir comprises at least about 2-10%, at least about 5-20%, at least about 5-15%, at least about 5-10%, at least about 7-8%, at least about 8-12%, at least about 10-20%, at least about 10-15%, or at least about 15-20% of one or more dissolving agents or permeation enhancer (all percentages in wt %). In other embodiments, the % weight of the dissolving agent or permeation enhancer in the drug reservoir layer is at least about 0.1% by weight relative to the weight of the entire reservoir, at least about 0.5%, at least about 1%, at least about 2%, at least about 3%, at least about 4%, at least about 5%, at least about 6%, at least about 7%, at least about 8%, at least about 9%, at least about 10%, at least about 11%, at least about 12%, at least about 13%, at least about 14%, at least about 15%, at least about 16%, at least about 17%, at least about 18%, at least about 19%, at least about 20%, at least about 25%, and typically less than about 50%, less than about 45%, less than about 30%, less than about 25%, less than about 20%, wherein all values are relative to the weight of the entire reservoir layer.

In some embodiments, the composition of either or both of the skin contact adhesive layer and the drug reservoir layer further comprises one or more permeation enhancers. A variety of permeation enhancers are known in the industry and are contemplated for use herein. Examples of the permeation enhancers for use in the compositions include, but are not limited to, methyl laurate, propylene glycol monolaurate, glycerol monolaurate, glycerol monooleate, lauryl lactate, myristyl lactate, and dodecyl acetate. Additional permeation enhancers are described in U.S. Pat. No. 8,874,879, which is incorporated herein by reference. It will be appreciated that the compositions herein may include one or more or at least one permeation enhancer.

In certain embodiments, the drug reservoir layer compositions further include one or more release-limiting agents. Representative examples of such release-limiting agents include, e.g., polycarbonates (e.g., linear polyesters of carbonic acids in which carbonate groups recur in the polymer chain), polyvinylchlorides, polyamides (e.g., polyhexamethylene adipamide, including NYLON); modacrylic copolymers (e.g., DYNEL); polysulfones; halogenated polymers (e.g., KYNAR); polyvinylfluoride (e.g., TEDLAR); polyfluorohalocarbon (e.g., ACLAR); polychlorethers (e.g., PENTON); acetal polymers (e.g., polyformaldehyde); acrylic resins (e.g., polyacrylonitrile polymethyl methacrylate, poly n-butyl methacrylate); polyurethanes, polyimides, polybenzimidazoles, polyvinyl acetate, aromatic and aliphatic, polyethers, cellulose esters (e.g., cellulose triacetate; cellulose; collodion); epoxy resins; olefins (e.g., polyethylene polypropylene); porous rubber; cross linked polyethylene oxide; cross-linked polyvinylpyrrolidone; cross-linked polyvinyl alcohol; polyelectrolyte structures formed of two ionically associated polymers of the type as set forth in U.S. Pat. Nos. 3,549,016 and 3,546,141. In other embodiments, the release-limiting agent includes derivatives of polystyrene such as polysodium styrenesulfonate and polyvinylbenzyltrimethyl-ammonium chloride; polyhydroxyethylmethacrylate; polyisobutylvinyl ether, and the like. A large number of copolymers which can be formed by reacting various proportions of monomers from the aforesaid said list of polymers are also useful for preparing the release-limiting agents utilized herein.

In certain embodiments, the release-limiting agents may also serve as disintegrants and/or dissolution enhancers. In embodiments, the disintegrant is polyvinylpyrrolidone (PVP), including cross-linked derivatives thereof such as polyvinylpolypyrrolidone (PVPP) and polyvinylpyrrolidone cross-linked material (PVP-CLM). In other embodiments, polyvinyl alcohol (PVA) or cross-linked polyvinyl alcohol (PVA) may also be employed. Preferably, the disintegrants are selected from polyvinylpyrrolidones having an average molecular weight of about 1,000 to 2,000,000 (e.g., KOLLIDON® 12 PF, KOLLIDON®17 PF, KOLLIDON® 25 PF, KOLLIDON® 30, KOLLIDON® 90; BASF Company), vinylpyrrolidone-vinyl acetate copolymers (such as KOLLIDON® VA 64; BASF Company), crosslinked polyvinylpyrrolidones (such as KOLLIDON® CL; BASF Company), polyvinyl alcohol, hydroxypropyl cellulose, ethyl cellulose, gelatin, starch (derivatives), dextrins and dextrans, such as, for example, α-, β- and γ-cyclodextrin, dimethyl-βcyclodextrin and 2-hydroxypropyl-β-cyclodextrin), sterols (such as cholesterol) or bile acids (such as cholic acid or lithocholic acid)

In some embodiments, the drug reservoir layer comprises at least about 5-30 wt % of one or more disintegrants relative to the weight of the adhesive matrix drug reservoir (inclusive of sub-ranges). In embodiments, the adhesive matrix drug reservoir comprises at least about 5-20%, at least about 5-15%, at least about 5-10%, at least about 10-30%, at least about 10-25%, at least about 10-20%, at least about 10-15%, at least about 12-18%, at least about 13-17%, at least about 15-30%, at least about 15-25%, or at least about 15-20% of one or more carriers (all percentages in wt %). In other embodiments, the adhesive matrix drug reservoir layer comprises at least about 4%, about 5%, about 6%, about 7%, about 8%, about 9%, about 10%, about 11%, about 12%, about 13%, about 14%, about 15%, about 16%, about 17%, about 18%, about 19%, about 20%, about 25%, about 26%, about 27%, about 28%, about 29%, about 30%, or greater, where all values are relative to the weight of the entire reservoir In certain embodiments, the drug reservoir composition may optionally further contain one or more surfactants. Examples of suitable additional surfactants include, for example, anionic surfactants, cationic surfactants, amphoteric surfactants, zwitterionic surfactants, non-ionic surfactants, and combinations thereof. Specific examples of suitable surfactants are known in the art and include those suitable for incorporation into compositions and wipes. The composition may suitably include one or more surfactants in an amount from about 0.01% by weight of the composition to about 2% by weight of the composition. When one or more surfactants is employed, the amount present in the compositions will vary depending on the particular surfactant chosen, the particular mode of administration (e.g., dermal or mucosal) and the effect desired.

The drug reservoir compositions may also further contain one or more additional emulsifiers. For example, natural fatty acids, esters and alcohols and their derivatives, and combinations thereof, may act as emulsifiers in the composition. Other examples of suitable emulsifiers include non-ionics such as polysorbate 20, polysorbate 80, anionics such as DEA phosphate, cationics such as behentrimonium methosulfate, and the like. The composition may suitably include one or more emulsifiers in an amount from about 0.01% by weight of the composition to about 2% by weight of the composition.

The present drug reservoir compositions may include one or more agents that increase viscosity chosen in quantities that preferably do not irritate the skin and increase the retention time. Preferred agents that increase viscosity include, but are not limited to, methylcellulose, carboxymethylcellulose sodium, ethylcellulose, carrageenan, carbopol, and/or combinations thereof. The most preferred agents used to increase viscosity and increase retention time is methylcellulose or carbopol. Typically, the agent that increases viscosity is added to the compositions in quantities of from about 0.1% to about 10% by weight.

The compositions of different embodiments may, of course, also include additional ingredients, such as acceptable surfactants, co-solvents, adhesives, agents to adjust the pH and osmolarity.

The drug reservoir composition may additionally include adjunct components conventionally found in pharmaceutical compositions in their art-established fashion and at their art-established levels. For example, the compositions may contain additional compatible pharmaceutically active materials for combination therapy, e.g., donepezil (ARICEPT®), rivastigmine (EXCELON®), galantamine (RAZADYNE®), icopezil, pyridostigmine, edrophonium, neostigmine, physostigmine, Huperzine A, phenserine, tacrine, including, L-type calcium channel blocker selected from amlodipine, felodipine, isradipine, lacidipine, lercanidipine, nicardipine, nifedipine, nimodipine, nitrendipine, nisoldipine, or (+) isopropyl 2-methoxyethyl 4-(2-chloro-3-cyano-phenyl)-1,4-dihydro-2,6-dimethylpyridine-3,5-dicarboxylate, or a combination thereof. See, U.S. pat. Pub. No. 2009/0156639.

In embodiments, the amount of each of the optional ingredients in the drug reservoir layer, e.g., permeation enhancers, gelling agents, emollients, surfactants, humectants, viscosity enhancers, emulsifiers, may individually range from about 0.1% to about 10% by weight of the entire reservoir, including, about 0.2%, about 0.4%, about 0.6%, about 0.8%, about 1.0%, about 1.5%, about 2.0%, about 2.5%, about 3.0%, about 3.5%, about 4.0%, about 4.5%, about 5.0%, about 6.0%, about 6.5%, about 7.0%, about 7.5%, about 8.0%, about 9.0%, about 10%, or greater % by weight, where all values are relative to the weight of the entire reservoir layer.

In certain embodiments, the compositions are pharmaceutical compositions comprising the memantine compound with a hydrophilic solvent carrier. The term "pharmaceutical composition" means for the present purposes any composition which comprises as an active compound, to which is attributed, fully or in part, the therapeutic (e.g., pharmaceutical) effect, at least one of the compounds or combinations thereof and that may optionally further comprise at least one pharmaceutically acceptable non-active ingredient, as an excipient, carrier or so.

In another embodiment, the pharmaceutical compositions are of pharmaceutical grade, e.g., formulated with the purity and consistency that is expected for clinical testing and/or medical use.

Particularly, the pharmaceutical compositions are of comparable potency compared to standard formulations or preparations containing memantine. In one embodiment, the standard formulation is a pharmaceutical composition containing memantine hydrochloride (e.g., NAMENDA). In one embodiment, the pharmaceutical composition has at least 60%, at least 70%, at least 80%, at least 90%, at least 95%, at least 99%, or greater potency compared to a standard formulation. Accordingly, the potency of the pharmaceutical compositions may be about 40%, about 41%, about 42%, about 43%, about 44%, about 45%, about 46%, about 47%, about 48%, about 49%, about 50%, about 51%, about 52%, about 53%, about 54%, about 55%, about 56%, about 57%, about 58%, about 59%, about 60%, about 61%, about 62%, about 63%, about 64%, about 65%, about 66%, about 67%, about 68%, about 69%, about 70%, about 71%, about 72%, about 73%, about 74%, about 75%, about 76%, about 77%, about 78%, about 79%, about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99%, about 99.9, or more compared to a pharmaceutical composition containing memantine hydrochloride (e.g., NAMENDA). Methods for determining potency of pharmaceutical preparations containing memantine, e.g., using in vitro NMDA receptor binding assays or in vivo anti-dementia activity assay, are known in the art.

In one embodiment, the drug reservoir composition is a dry composition. In another embodiment, the drug reservoir composition is a semi-solid or a gel composition.

A drug reservoir comprised of a composition as described herein and hereinabove is contemplated for use in a transdermal delivery system, where the system additionally comprises a skin contact adhesive. In embodiments, the transdermal delivery systems contemplated herein are configured to transdermally deliver an active agent, specifically memantine, to a subject when topically applied to a skin surface of a subject. In some embodiments, the systems and compositions are formulated to provide for multi-day delivery of a therapeutically effective amount of memantine to a subject when the composition is topically applied to said subject. By multi-day delivery is meant that the layer is formulated to provide a therapeutically effective amount to a subject when the composition is applied to a skin site of a subject for a period of time that is about 1 day, about 2 days, about 3 days, about 4 days, about 5 days, about 6 days, about 7 days, about 8 days, about 9 days, about 10 days or more, e.g., 2 weeks. By therapeutically effective amount is meant that the compositions, when applied to a skin site of a subject during its intended time of application, e.g., within 3 days or within 7 days of application, provides for a systemic amount of memantine that provides a desired therapeutic activity. In some embodiments, the compositions provide delivery of a target dosage of active agent that is about 1.0 mg/day over a 3-day period (i.e., 3 days; 72 hours). In other embodiments, over the same 3-day period, the target dosage of the active agent is about 3 mg/day, about 5 mg/day, about 8 mg/day, about 10 mg/day, about 12 mg/day, about 15 mg/day, about 20 mg/day, about 25 mg/day, about 30 mg/day, or more. In a related embodiment, the compositions provide delivery of a target dosage of active agent that is about 7.0 mg/day over a 1 week period (i.e., 7 days; 168 hours). In other embodiments, over the same 7-day period, the target dosage of the active agent is about 3 mg/day, about 5 mg/day, about 8 mg/day, about 10 mg/day, about 12 mg/day, about 15 mg/day, about 20 mg/day, about 25 mg/day, about 30 mg/day, or more.

Transdermal compositions according to certain embodiments of the present disclosure exhibit a therapeutically sufficient skin flux of memantine over an extended period of time. A therapeutically sufficient flux of memantine over an extended period of time may be defined such that the average delivery flux on the first day should not be greater than a fixed criterion from the average daily flux on the last day of wear, for example, day 1 and day 3 or day 1 and day 7. The fixed criterion can vary, ranging from a factor of 5 to a factor of 1, such as a factor of 4 to a factor of 1.25, where in some instances the fixed criterion is a factor of 3, or a factor of 2 or a factor of 1.5. The extended period of time over which substantially the flux is observed may vary, and in some instances is 24 hours or longer, such as 48 hours or longer, including 72 hours or longer, e.g., 96 hours or longer, including 120 hours or longer, such as 144 hours or longer, e.g., 168 hours or longer, including 240 hours or longer. While the actual flux may vary, in some instances skin permeation rates of at least about 1 $\mu g/cm^2/hr$, e.g., about 4 $\mu g/cm^2/hr$, about 5 $\mu g/cm^2/hr$, about 6 $\mu g/cm^2/hr$ or more are provided by the compositions, including, a flux of about 40 $\mu g/cm^2/hr$ or less, such as 20 $\mu g/cm^2/hr$ or less.

In certain aspects, the therapeutic skin flux ranges from 1 to 40 $\mu g/cm^2/hr$, such as from 1 to 20 $\mu g/cm^2/hr$, such as from 2 to 20 $\mu g/cm/hr$, such as from 2 to 15 $\mu g/cm^2/hr$, including from 4 to 15 $\mu g/cm^2/hr$ or 5 to 15 $\mu g/cm^2/hr$, e.g., for an extended period of time (e.g., from 2 to 10 days, including 5 or more days, e.g., 7 or more days). In some embodiments, the devices, systems and compositions described herein provide an in vitro memantine skin flux of between about 1-35 $\mu g/cm^2/hr$, 1-30 $\mu g/cm^2/hr$, 1-25 $\mu g/cm^2/hr$, 1-20 $\mu g/cm^2/hr$, 1-15 $\mu g/cm^2/hr$, 1-12 $\mu g/cm^2/hr$, 1-10 $\mu g/cm^2/hr$, 1-7.5 $\mu g/cm^2/hr$, 1-5 $\mu g/cm^2/hr$, 2-40 $\mu g/cm^2/hr$, 2-35 $\mu g/cm^2/hr$, 2-30 $\mu g/cm^2/hr$, 2-25 $\mu g/cm^2/hr$, 2-20 $\mu g/cm^2/hr$, 2-15 $\mu g/cm^2/hr$, 2-12 $\mu g/cm^2/hr$, 2-10 $\mu g/cm^2/hr$, 2-7.5 $\mu g/cm^2/hr$, 2-5 $\mu g/cm^2/hr$, 4-40 $\mu g/cm^2/hr$, 4-35 $\mu g/cm^2/hr$, 4-30 $\mu g/cm^2/hr$, 4-25 $\mu g/cm^2/hr$, 4-20 $\mu g/cm^2/hr$, 4-15 $\mu g/cm^2/hr$, 4-12 $\mu g/cm^2/hr$, 4-10 $\mu g/cm^2/hr$, 4-7.5 $\mu g/cm^2/hr$, 4-5 $\mu g/cm^2/hr$, 5-40 $\mu g/cm^2/hr$, 5-35 $\mu g/cm^2/hr$, 5-30 $\mu g/cm^2/hr$, 5-25 $\mu g/cm^2/hr$, 5-20 $\mu g/cm^2/hr$, 5-15 $\mu g/cm^2/hr$, 5-12 $\mu g/cm^2/hr$, 5-10 $\mu g/cm^2/hr$, 5-7.5 $\mu g/cm^2/hr$, 10-40 $\mu g/cm^2/hr$, 10-35 $\mu g/cm^2/hr$, 10-30 $\mu g/cm^2/hr$, 10-25 $\mu g/cm^2/hr$, 10-20 $\mu g/cm^2/hr$, 10-15 $\mu g/cm^2/hr$, 10-12 $\mu g/cm^2/hr$, 15-40 $\mu g/cm^2/hr$, 15-35 $\mu g/cm^2/hr$, 15-30 $\mu g/cm^2/hr$, 15-25 $\mu g/cm^2/hr$, 15-20 $\mu g/cm^2/hr$, 20-40 $\mu g/cm^2/hr$, 20-35 $\mu g/cm^2/hr$, 20-30 $\mu g/cm^2/hr$, 20-25 $\mu g/cm^2/hr$, 30-40 $\mu g/cm^2/hr$, or 30-35 $\mu g/cm^2/hr$ for a period of at least about 1-10 days. In embodiments, the transdermal devices for systems provide the above skin flux for a period of about 1-5 days, about 2-5 days, about 2-10 days, or about 5-10 days. In embodiments, the transdermal devices for systems provide the above skin flux for a period of about 1, 2, 3, 4, 5, 6, 7, 8, 9, or 10 days.

Transdermal compositions as described herein provide for desirable $C_{min}/C_{max}$. $C_{min}/C_{max}$ refers to the minimum plasma level of memantine over maximum over a wear period (e.g., 3 or more days, such as 5 or more days, including 7 or more days) and is a measure of the depletion of memantine from the topical formulation over the wear period. If $C_{min}/C_{max}$ is low, a conclusion can be made that the topical formulation is not retaining the drug administration during wear period, and blood concentration is continuing to decrease over the wear period. In some instances, the topical formulations provide a $C_{min}/C_{max}$ of at least about 0.4, about 0.5, about 0.6, about 0.7, wherein in some instances, the $C_{min}/C_{max}$ is 1.0 or lower, such as 0.8 or lower, e.g., 0.6 or lower.

In embodiments, the system further comprises a skin contact adhesive layer.

The size (i.e., area) of the transdermal devices and systems or any layer thereof may vary according to need and/or composition. In certain embodiments, the size of the composition is chosen in view of the desired transdermal flux rate of the active agent and the target dosage. For example, if the transdermal flux is 40 µg/cm$^2$/hr and the target dosage is 12 mg/day, then the transdermal composition may have an area of ranging from 5 to 15 cm$^2$. Or for example, if the transdermal flux is 20 µg/cm$^2$/hr and the target dosage is 6 mg/day, then the transdermal patch may have an area ranging from 5 to 15 cm$^2$. In certain aspects, the compositions have dimensions in order to cover an area of skin when applied to a skin site that ranges from 10 to 200 cm$^2$, such as 20 to 150 cm$^2$, including 40 to 140 cm$^2$, e.g., 60 cm$^2$. According to certain embodiments, the dimensions of the active agent layer range from 5 to 75 cm$^2$, such as from 15 to 60 cm$^2$, such as from 10 to 50 cm$^2$, including from 20 to 50 cm$^2$, e.g., 20 to 40 cm$^2$, including 35 cm$^2$.

The memantine-containing active agent layer of the compositions may vary in coat weight. In some instances, the coat weight of the active agent layer ranges from 2.5 mg/cm$^2$ to 100 mg/cm$^2$, such as from 2.5 mg/cm$^2$ to 50 mg/cm$^2$, such as 5 mg/cm$^2$ to 20 mg/cm$^2$, e.g., 7.5 mg/cm$^2$ to 15 mg/cm$^2$, including 9 mg/cm$^2$ to 12 mg/cm$^2$ in coat weight. Since the difficulty and cost in manufacturing increases with thicker active agent layers and yet thicker layers allow for less depletion of drug and hence less decreasing flux during wear, in some instances a coat weight that represents a balance of these parameters is employed, e.g., a coat weight ranging from 10 to 90 mg/cm$^2$, such as 20 to 70 mg/cm$^2$, and including 25 to 50 mg/cm$^2$.

An aspect of the transdermal compositions according to certain embodiments of the present disclosure is that they are storage stable. By storage-stable is meant that the compositions may be stored for extended periods of time without significant degradation, loss and/or significant reduction in activity of the memantine. In certain embodiments, the subject compositions are stable for 6 months or longer, such as 1 year or longer, including 18 months or longer, 2 years or longer, e.g., 3 years or longer, etc., when maintained at 25° C. and 60% relative humidity (RH) as defined in the WHO technical Report Series No. 953 (2009). In some cases, the ratio of the amount of memantine in the composition to the initial amount of memantine in the composition after storage at about 60° C. for at least one month is 50% or more, 60% or more, such as 70% or more, including 80% or more, or greater, including 90% or greater, 95% or greater, 98% or greater, including 99% or greater, in some instances up to 100% or greater to account for experimental error and variation in coating.

The term "system," as used herein, is defined as an article, an apparatus or a device containing the memantine compound or a composition thereof for administration to the skin, local tissues under the skin, the circulation system or other sites or targeting the human body via skin permeation sites.

In some instances, the transdermal compositions are configured as a single layer composition. By "single layer" is meant that the transdermal delivery device includes only a single layer of active agent containing matrix and does not include separate distinct layers for the pressure sensitive adhesive, transdermal active agent layer, etc. Likewise, single layer transdermal delivery devices do not further include a separate active agent reservoirs (i.e., an active agent reservoir) separate from the pressure sensitive adhesive. As such, single layer transdermal compositions may include in a single matrix an amount of each of the components of the transdermal compositions necessary for practicing the subject methods, as described in greater detail below. For example, in some embodiments, single layer transdermal compositions of interest include a single layer matrix of memantine and an adhesive. According to some embodiments, the compositions of the present disclosure include a backing, and a memantine-containing active agent layer. The composition may further include a release liner.

In one embodiment, the delivery systems comprise a multi-layer. As used herein, the term "multi-layer" refers to two or more layers of polymer, copolymer, blend of polymers, blend of copolymers, of any combination thereof, which has at least a first bottom layer and a second top layer. As a representative example, a multi-layered patch may contain another layer of drug-in-adhesive, usually separated by a membrane (but not in all cases) from other layers. This way, one layer may provide immediate release of the drug and another layer may provide control release of drug from the reservoir. Multi-layered patches may optionally contain a temporary liner-layer and a permanent backing. The rate of drug release from the various layers depends on membrane permeability and diffusion of drug molecules. One representative example of a multi-layered patch is provided in FIG. 1B.

In one exemplary drug reservoir layer, a matrix that comprises or consists essentially of memantine base generated in situ by reaction of memantine HCl and sodium bicarbonate; a permeation enhancer of octyldodecanol and glycerol as a carrier; and a polymeric, adhesive matrix of crosslinked polyvinylpyrrolidone and a copolymer of acrylic acid/vinyl acetate is contemplated. In another exemplary drug reservoir comprising an adhesive matrix that comprises or consisting essentially of memantine base generated in situ by reaction of between about 10-30 wt % memantine HCl and between about 5-15 wt % sodium bicarbonate; about 5-15 wt % octyldodecanol; about 5-15 wt % glycerol; about 5-30 wt % crosslinked polyvinylpyrrolidone; and about 20-50 wt % acrylate-vinylacetate copolymer is contemplated. In yet another example, a composition comprising a drug reservoir consisting essentially of memantine base generated in situ by reaction of between about 20-30 wt % memantine HCl and between about 8-10 wt % sodium bicarbonate; about 8-12 wt % octyldodecanol; about 8-12 wt % glycerol; about 13-17 wt % crosslinked polyvinylpyrrolidone; and about 30-35 wt % acrylate-vinylacetate copolymer is contemplated.

A drug reservoir comprised of a composition as described herein and hereinabove is contemplated for use in a transdermal delivery system, where the system additionally comprises a skin contact adhesive. The skin contact adhesive layer may be fabricated from any of the adhesive materials listed herein. In one embodiment, the skin contact adhesive comprises a higher alcohol and a biocompatible polymer. In one embodiment, the skin contact adhesive excludes the hydrophilic solvent carrier present in the drug reservoir, and in one embodiment excludes glycerol.

In one embodiment, the skin contact adhesive layer comprises a $C_{10-30}$ higher alcohol. Particularly, the higher alcohol is selected from the group consisting of lauryl alcohol, isostearyl alcohol, octyldodecanol, and oleyl alcohol.

In one embodiment, the amount of the higher alcohol, e.g., octyldodecanol, in the skin contact adhesive layer is at least about 0.5 or 1% by weight relative to the weight of the adhesive layer, including, at least about 4%, e.g., about 5%, about 6%, about 7%, about 8%, about 9%, about 10%, about 11%, about 12%, about 13%, about 14%, about 15%, about 16%, about 17%, about 18%, about 19%, about 20%, or greater % by weight, and typically less than about 50%, less than about 45%, less than about 30%, less than about 25%, or less than about 20% or less than about 15%, wherein all values are relative to the weight of the adhesive layer. Particularly, the % weight of the higher alcohol in the adhesive layer is between about 1-25 wt %, 5-20 wt %, 5%-15%, especially about 8%-12%, of the entire adhesive layer.

In one embodiment, the skin contact adhesive layer comprises one or more biocompatible polymers selected from one or more of polyisobutylene (PIB), a silicone polymer, acrylate copolymers, butyl rubber, polybutylene, styrene-iosprene-styrene block copolymers, styrene-butadiene-styrene block copolymers, ethylene-vinyl acetate (EVA), mixtures and copolymers thereof. In one embodiment, the biocompatible polymer is polyisobutylene.

In one embodiment, the biocompatible polymer is a PIB-based matrix comprising PIB Oppanol B100 (BASF, MW=1,100,000), PIB Oppanol B 12 (BASF, MW=51,000, MW/MN=3.2) and polybutene (PB) Indopol H1900 (INEOS oligomers, MW=4500, MW/MN=1.8). The weight ratio between components of the PIB matrix is as follows: PIB Oppanol B100:PIB Oppanol B 12:Indopol H1900=10:50:40 (See, Brantseva et al., European Polymer Journal, 76, 228-244, 2016).

In one embodiment, the skin contact adhesive layer comprises a biocompatible polymer, containing about 40%, about 41%, about 42%, about 43%, about 44%, about 45%, about 46%, about 47%, about 48%, about 49%, about 50%, about 51%, about 52%, about 53%, about 54%, about 55%, about 56%, about 57%, about 58%, about 59%, about 60%, about 61%, about 62%, about 63%, about 64%, about 65%, about 66%, about 67%, about 68%, about 69%, about 70%, about 71%, about 72%, about 73%, about 74%, about 75%, about 76%, about 77%, about 78%, about 79%, about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99%, about 99.9, or greater % by weight, wherein all values are relative to the weight of the adhesive layer. Particularly, the % weight of the biocompatible polymer in the adhesive layer is between about 50%-95%, especially about 60%-80%, of the entire skin contact adhesive layer. In some embodiments, the amount of the biocompatible polymer in the skin contact adhesive layer is at least about 50-90%, 50-85%, 50-80%, 50-75%, 50-70%, 50-65%, 50-60%, 50-55%, 55-95%, 55-90%, 55-85%, 55-80%, 55-75%, 55-70%, 55-65%, 55-60%, 60-95%, 60-90%, 60-85%, 60-80%, 60-75%, 60-70%, 60-65%, 65-95%, 65-90%, 65-85%, 65-80%, 65-75%, 65-70%, 70-95%, 70-90%, 70-85%, 70-80%, 70-75%, 75-95%, 75-90%, 75-85%, 75-80%, 80-95%, 80-90%, 80-85%, 85-95%, 85-90%, or 90-95%.

In some embodiments, the skin contact adhesive layer optionally comprises highly dispersive silica, e.g., hydrophobic colloidal silica that can effectively adsorb hydrophobic drugs and other hydrophobic ingredients. By using hydrophobic colloidal silica at a certain percentage as an excipient (from about 3% to about 20%, preferably from about 5% to about 10% in the formulation), the diffusion of the active ingredient through the matrix can be controlled during storage. Examples of the dispersive silica for use in the compositions include, but are not limited to, the high purity amorphous anhydrous colloidal silicon dioxide for use in pharmaceutical products sold under the name AEROSIL, e.g., AEROSIL®90, AEROSIL®130, AEROSIL®150, AEROSIL®200, AEROSIL®300, AEROSIL®380, AEROSIL®OX50, AEROSIL®TT600, AEROSIL®MOX80, AEROSIL®COK84, AEROSIL®R202, AEROSIL®R805, AEROSIL®R812, AEROSIL®812S, AEROSIL®R972, and/or AEROSIL® R974 or any other highly disperse silica, especially AEROSIL®200 and/or AEROSIL®R972 can be used as highly disperse silica.

In one embodiment, the skin contact adhesive layer comprises highly dispersive silica at least about 40% by weight relative to the weight of the entire adhesive layer, including, at least about 1% by weight relative to the weight of the adhesive layer, including, at least about 3%, e.g., about 4%, about 5%, about 6%, about 7%, about 8%, about 9%, about 10%, about 11%, about 12%, about 13%, about 14%, about 15%, about 16%, about 17%, about 18%, about 19%, about 20%, or greater % by weight, wherein all values are relative to the weight of the entire adhesive layer.

In some embodiments, the skin contact adhesive layer optionally comprises one or more matrix modifiers. Without wishing to be bound by theory, it is believed that the matrix modifier facilitates homogenization of the adhesive matrix. Sorption of hydrophilic moieties is a possible mechanism for this process. Thus, known matrix modifiers which are to some degree water-sorbent may be used. For example, possible matrix modifiers include colloidal silicone dioxide, fumed silica, cross-linked polyvinylpyrrolidone (PVP), soluble PVP, cellulose derivatives (e.g. hydroxypropyl cellulose (HPC), hydroxyethylcellulose (HEC)), polyacrylamide, polyacrylic acid, a polyacrylic acid salt, or a clay such as kaolin or bentonite. An exemplary commercial fumed silica product is Cab-O-Sil (Cabot Corporation, Boston, Mass.). The hydrophilic mixtures described in U.S. Published Patent Application No. 2003/0170308 may also be employed, for example mixtures of PVP and PEG or of PVP, PEG, and a water-swellable polymer such as EUDRAGIT® L100-55.

In embodiments, the matrix modifier is individually included in an amount between about 1-40%, about 10-30%, about 15-25%, about 5-7%, about 7-20%, or about 7-25% relative to the weight of the adhesive matrix (inclusive of sub-ranges), including, at least about 3%, e.g., about 4%, about 5%, about 6%, about 7%, about 8%, about 9%, about 10%, about 11%, about 12%, about 13%, about 14%, about 15%, about 16%, about 17%, about 18%, about 19%, about 20%, or greater % by weight, wherein all values are relative to the weight of the entire adhesive contact layer. In some embodiments, the matrix modifier does not include ethylcellulose. In some embodiments, the amount of the matrix modifier in the skin contact adhesive layer is at least about 1-35%, 1-30%, 1-25%, 1-20%, 1-15%, 1-10%, 1-5%, 5-40%, 5-35%, 5-30%, 5-25%, 5-20%, 5-15%, 5-10%, 10-40%, 10-35%, 10-30%, 10-35%, 10-20%, 10-30%, 10-35%, 10-25%, 10-20%, 10-15%, 15-40%, 15-35%, 15-30%, 15-25%, 15-20%, 20-40%, 20-35%, 20-30%, 20-25%, 25-40%, 25-35%, 25-30%, 30-40%, 30-35%, or 35-40%.

In some embodiments, the hydrophobic drug (e.g., memantine) and other hydrophobic ingredients may be adsorbed to the hydrophobic surface of the silica particles using art-known technology. In such embodiments, the hydrophobic colloidal silica has a large specific surface area for drug deposition, as well as exhibiting strong adsorption to hydrophobic drugs.

In one embodiment, the adhesive contact layer comprises at least one higher alcohol, at least one biocompatible polymer and at least one matrix modifier (without dispersive silicate). In another embodiment, the adhesive contact layer comprises at least one higher alcohol, at least one biocompatible polymer, and dispersive silica (without the matrix modifier). In other embodiments, the adhesive contact layer contains at least one higher alcohol, at least one biocompatible polymer, the matrix modifier and dispersive silica.

The skin contact adhesive layer may also comprise at least one permeation enhancer, and a variety of such enhancers are known in the industry and described above. In embodiments, the skin contact adhesive layer comprises as a permeation enhancer one or more of triethyl citrate, sorbitan monolaurate, and/or lauryl lactate.

The penetration or permeation enhancer in either or both of the skin contact adhesive layer and the drug reservoir adhesive matrix layer may be chosen from a wide range of such compounds known in the art. In some embodiments, permeation enhancers for use in the adhesive matrix include, but are not limited to, methyl laurate, propylene glycol monolaurate, glycerol monolaurate, glycerol monooleate, lauryl lactate, myristyl lactate, and dodecyl acetate. In some embodiments, the permeation enhancer is selected from triethyl citrate, sorbitan monolaurate, an α-hydroxy acid enhancer (e.g., an ester of lactic acid or glycolic acid, i.e., lauryl lactate) may also be included. Additional permeation enhancers are described in U.S. Pat. No. 8,874,879, which is incorporated herein by reference. It will be appreciated that the compositions herein may include one or more or at least one permeation enhancer. In embodiments, the penetrating or permeating enhancer is included in an amount between about 1-10%, about 2-5%, about 2-10% relative to the weight of the adhesive matrix.

In one embodiment, the skin contact adhesive layer as manufactured does not include a pharmaceutically active agent intended for systemic delivery. For example, the ingredients combined to form the skin contact adhesive layer do not include memantine base or a memantine salt. However, the skin contact adhesive layer when fabricated into a transdermal delivery system and stored for a period of time and/or during use may contain the pharmaceutically active agent intended for systemic delivery because the agent may diffuse from the drug reservoir adhesive matrix into the skin contact adhesive layer.

Either or both of the skin contact adhesive layer and the drug reservoir adhesive matrix may further include other conventional additives such as adhesive agents, antioxidants, crosslinking or curing agents, pH regulators, pigments, dyes, refractive particles, conductive species, antimicrobial agents, opacifiers, gelling agents, viscosity modifiers or thickening agents, stabilizing agents, and the like as known in the art. In those embodiments wherein adhesion needs to be reduced or eliminated, conventional detackifying agents may also be used. Other agents may also be added, such as antimicrobial agents, to prevent spoilage upon storage, i.e., to inhibit growth of microbes such as yeasts and molds. Suitable antimicrobial agents are typically selected from the group consisting of the methyl and propyl esters of p-hydroxybenzoic acid (i.e., methyl and propyl paraben), sodium benzoate, sorbic acid, imidurea, and combinations thereof. These additives, and amounts thereof, are selected in such a way that they do not significantly interfere with the desired chemical and physical properties of the adhesive and/or active agent.

Either or both of the skin contact adhesive layer and the drug reservoir adhesive matrix may further may also contain irritation-mitigating additives to minimize or eliminate the possibility of skin irritation and/or skin damage resulting from the drug, the enhancer, or other components of the composition. Suitable irritation-mitigating additives include, for example: α-tocopherol; monoamine oxidase inhibitors, particularly phenyl alcohols such as 2-phenyl-1-ethanol; glycerin; salicylic acids and salicylates; ascorbic acids and ascorbates; ionophores such as monensin; amphiphilic amines; ammonium chloride; N-acetylcysteine; cis-urocanic acid; capsaicin; chloroquine; and corticosteriods.

Figure 1B:
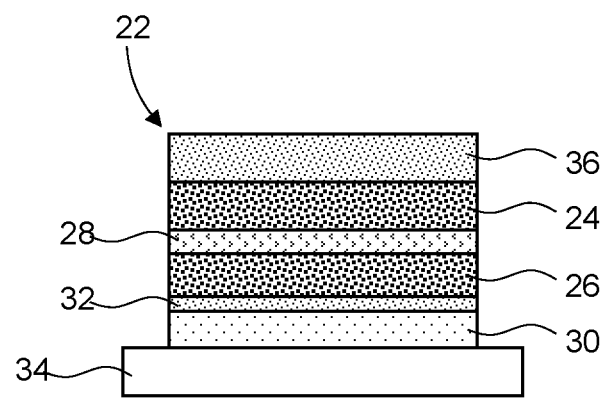
Figure 1C:
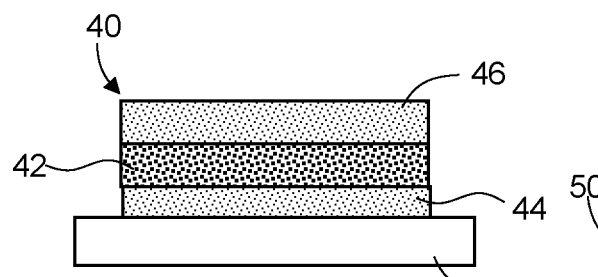

A transdermal delivery system comprised of a drug reservoir and a skin contact adhesive can have a variety of configurations, and several non-limiting examples are depicted in are set forth in FIGS. 1A-1D. FIG. 1A illustrates a transdermal delivery system 10 comprised of a drug reservoir 12 and a contact adhesive 14 separated by a rate controlling membrane or by a non-rate controlling material, such as a tie layer composed of a non-woven polyester or polypropylene, 16. A backing layer 18 and a release liner 20 are also present. FIG. 1B illustrates a second embodiment of a transdermal delivery system 22 comprised of a first drug reservoir 24 and a second drug reservoir 26, the first and second drug reservoirs separated by a non-rate controlling material, such as a tie layer composed of a non-woven polyester or polypropylene, 28. A contact adhesive layer 30 provides for attachment of the system to the skin of a user, where a rate controlling membrane 32 controls release of therapeutic agent from the second drug reservoir into the contact adhesive and ultimately onto the skin of a user. A release liner 34 and a backing layer 36 are also present. FIG. 1C shows another embodiment of a transdermal delivery system 40 comprised of a drug reservoir 42 and a contact adhesive layer 44 that provides for attachment of the system to the skin of a user. A backing layer 46 and a release liner 48 are also present.

Figure 1D:
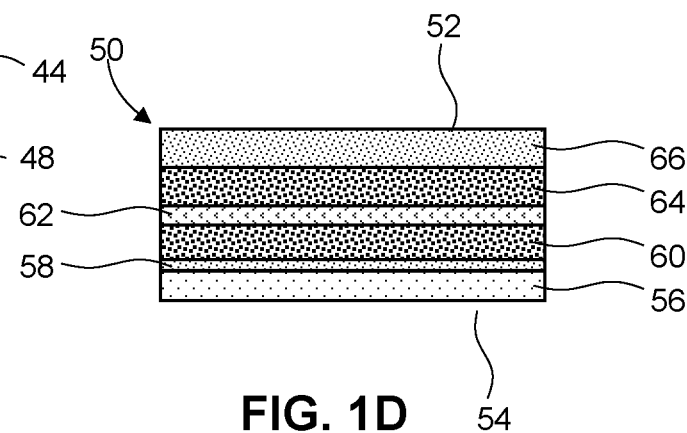

FIG. 1D shows another embodiment of a transdermal delivery system for systemic delivery of memantine base. The system 50 comprises, in series from the skin facing side 54 to the external environment facing side 52, a skin contact adhesive layer 56 to attach the system to the skin of a user. In one embodiment, the skin contact adhesive layer manufactured is manufactured from an adhesive formulation that does not comprise memantine base or a memantine salt. Directly in contact with the skin contact adhesive layer is an intermediate layer 58. The intermediate layer can be, for example, a non-woven polyester material or a drug rate-controlling membrane, such as a microporous polyethylene or polyprolylene. The intermediate layer has opposing sides, a skin-facing side (that is in contact with the skin contact adhesive layer 54) and an environment facing side. On the environment facing side of the intermediate layer is an adhesive matrix drug reservoir layer 60. The drug reservoir layer is manufactured with an adhesive material, memantine HCl and an alkaline salt. The latter two components react in situ to generate memantine base in the drug reservoir layer that is delivered to the user after application of the system to the skin. In contact with the adhesive matrix drug reservoir layer 60 is a first backing layer 62, and in contact with the first backing layer is an adhesive overlay 64. A second backing layer 66 is in contact with the adhesive overlay and with the environment. In one embodiment, the adhesive overlay 64 is composed of two different adhesive layers—for example a first layer of polyisobutylene and polybutene, with or without a crosslinked polyvinylpyrrolidone, and a second layer of an acrylic adhesive.

Accordingly, in one embodiment a transdermal delivery system for systemic delivery of memantine base is provided. The system comprises, in series from the skin facing side to the external environment, a skin contact adhesive layer to attach the system to the skin of a user, the skin contact adhesive layer optionally manufactured from an adhesive formulation that does not comprise memantine base or a memantine salt. Directly in contact with the skin contact adhesive layer is an intermediate layer. On the opposing surface of the intermediate layer is a drug reservoir layer comprised of (i) an acrylate copolymer, (ii) octyldodecanol and glycerol, and (iii) memantine base generated in situ by reaction of memantine HCl and an alkaline salt. In contact with the drug reservoir layer is a first backing layer, and optionally in contact with the first backing layer is an adhesive overlay. An optional second backing layer is in contact with the adhesive overlay and with the environment.

The intermediate layer, also referred to as a fabric layer, a membrane or a tie layer, may be formed of any suitable material including, but not limited to, polyesters, vinyl acetate polymers and copolymers, polyethylenes, and combinations thereof. In one embodiment, the intermediate layer is a nonwoven layer of polyester fibers such as the film sold under the name Reemay® (Kavon Filter Products Co.). In embodiments, the intermediate layer does not affect the rate of release of the active agent from the adhesive layers. In another embodiment, the intermediate layer is a rate controlling membrane for memantine base. For example, the rate controlling membrane can be a microporous polypropylene or polyethylene.

In one embodiment, the intermediate layer is a microporous membrane comprising a plurality of pores. In exemplary transdermal systems prepared as described in the working examples, the plurality of pores in the microporous membrane contains a single solvent or a solvent composition. In one embodiment, the solvent composition in the pores of the microporous membrane is comprised of one or more of the solvents present in either or both of the drug reservoir and the contact adhesive. However, in one embodiment, the plurality of pores in the microporous membrane does not contain the hydrophilic solvent carrier present in the drug reservoir. An exemplary solvent composition contained in the pores of the microporous membrane is one or more of a permeation enhancer and a surfactant. Exemplary solvents include triethyl citrate and octyldodecanol. An exemplary embodiment is that the pores of the microporous membrane are filled or partially filled or contain or partially contain the solvent octadodecanol. In one embodiment, contained in the pores of the microporous membrane is a single solvent octadodecanol. The microporous membrane may be pretreated with the solvent or solvent composition so that its pores are saturated with, filled with, or partially filled with the solvent or solvent composition. The microporous membrane is, in one embodiment, a polypropylene microporous membrane and may have an average pore size in the range of about 0.001 µm to about 100 µm, about 1 µm to about 10 µm, about 0.010 µm to about 0.100 µm, or about 0.040 µm to about 0.050 µm. For example, the average pore size can be about 0.035 µm, 0.036 µm, 0.037 µm, 0.038 µm, 0.039 µm, 0.040 µm, 0.041 µm, 0.042 µm, 0.043 µm, 0.044 µm, 0.045 µm, 0.046 µm, 0.047 µm, 0.048 µm, 0.049 µm, or 0.050 µm. In some embodiments, the microporous membrane has an average pore size of about 0.043 µm. The microporous membrane is, in one embodiment, a polypropylene microporous membrane and has a porosity in the range of about 30% to about 50%, about 35% to about 45%, or about 40% to about 42%. For example, the microporous membrane can have a porosity of about 30%, 31%, 32%, 33%, 34%, 35%, 36%, 37%, 38%, 39%, 40%, 41%, 42%, 43%, 44%, 45%, 46%, 47%, 48%, 49%, or 50%.

The adhesive overlay in the delivery system of FIG. 1D is comprised, in one embodiment, of a polyisobutylene and polybutene mixture. In another embodiment, the adhesive overlayer is comprised of a first layer and a second layer, the first layer composed of a polyisobutylene, polybutene and crosslinked polyvinylpyrrolidone mixture and the second layer composed of an acrylic adhesive. Polyisobutylene is a vinyl polymer comprised of the isobutylene monomer. Polybutene is a viscous, non-drying, liquid polymer, prepared by copolymerization of 1- and 2-butene with a small quantity of isobutylene. In some embodiments, the polybutene in one embodiment has a molecular weight of between about 750-6000 Daltons, preferably between about 900-4000 Daltons, and preferably between about 900-3000 Daltons. In some embodiments the mixture comprises polybutene in the polyisobutylene blend at about 40 weight percent. More generally, the polybutene is present in the polyisobutylene blend in an amount between 20-50 weight percent, or between 25-45 weight percent. In another embodiment, the adhesive overlayer is a single layer and comprised of an acrylate copolymer that forms the single layer adhesive overlay. An exemplary acrylate copolymer is DuroTak® 387-2052.

In embodiments, the transdermal delivery system comprises at least one backing layer that provides a structural element for holding or supporting the underlying adhesive layer(s). The backing layer may be formed of any suitable material as known in the art. In some embodiments, the backing layer is occlusive. In some embodiments, the backing is preferably impermeable or substantially impermeable to moisture. In one exemplary embodiment, the barrier layer has a moisture vapor transmission rate of less than about 50 $g/m^2$-day. In some embodiments, the backing layer is preferably inert and/or does not absorb components of the adhesive layer, including the active agent. In some embodiments, the backing layer preferably prevents release of components of the adhesive layer through the backing layer. The backing layer may be flexible or nonflexible. The backing layer is preferably at least partially flexible such that the backing layer is able to conform at least partially to the shape of the skin where the patch is applied. In some embodiments, the backing layer is flexible such that the backing layer conforms to the shape of the skin where the patch is applied. In some embodiments, the backing layer is sufficiently flexible to maintain contact at the application site with movement, e.g. skin movement. Typically, the material used for the backing layer should permit the device to follow the contours of the skin or other application site and be worn comfortably on areas of skin such as at joints or other points of flexure, that are normally subjected to mechanical strain with little or no likelihood of the device disengaging from the skin due to differences in the flexibility or resiliency of the skin and the device.

In some embodiments, the backing layer is formed of one or more of a film, non-woven fabric, woven fabric, laminate, and combinations thereof. In some embodiments, the film is a polymer film comprised of one or more polymers. Suitable polymers are known in the art and include elastomers, polyesters, polyethylene, polypropylene, polyurethanes and polyether amides. In some embodiments, the backing layer is formed of one or more of polyethylene terephthalate, various nylons, polypropylene, metalized polyester films, polyvinylidene chloride, and aluminum foil. In some embodiments, the backing layer is a fabric formed of one or more of polyesters such as polyethylene terephthalate, polyurethane, polyvinyl acetate, polyvinylidene chloride and polyethylene. In one particular, but non-limiting embodiment, the backing layer is formed of a polyester film laminate. One particular polyester film laminate is the polyethylene and polyester laminate such as the laminate sold under the name SCOTCHPAK™ #9723.

In embodiments, the device includes a release liner at least partially in contact at least with the contact adhesive layer to protect the adhesive layer prior to application. The release liner is typically a disposable layer that is removed prior to application of the device to the treatment site. In some embodiments, the release liner preferably does not absorb components of the adhesive layer, including the active agent. In some embodiments, the release liner is preferably impermeable to components of the adhesive layer (including the active agent) and prevents release of components of the adhesive layer through the release liner. In some embodiments, the release liner is formed of one or more of a film, non-woven fabric, woven fabric, laminate, and combinations thereof. In some embodiments, the release liner is a silicone-coated polymer film or paper. In some non-limiting embodiments, the release liner is a silicone-coated polyethylene terephthalate (PET) film, a fluorocarbon film, or a fluorocarbon coated PET film.

The thickness and/or size of the device and/or adhesive matrices may be determined by one skilled in the art based at least on considerations of wearability and/or required dose. It will be appreciated that the administration site for the device will affect the wearability considerations due to the available size of the administration site and the use of the administration site (e.g. need for flexibility to support movement). In some embodiments, the device and/or adhesive matrix has a thickness of between about 25-500 µm. In some embodiments, the device and/or adhesive matrix has a thickness of between about 50-500 µm. In some embodiments, the patch has a size in the range of about 16 cm$^2$-225 cm$^2$. It will be appreciated that the thickness and size provided here are merely exemplary and the actual thickness and or size may be thinner/smaller or thicker/larger as needed for a specific formulation.

As discussed herein, the patch device (e.g., the patch devices in FIGS. 1A-1D) can further comprise at least one additional non-adhesive polymeric environment, e.g., a backing layer. This layer is disposed adjacent to the adhesive polymeric diffusion environment and functions to facilitate the delivery of the active ingredient to the skin. This additional layer may comprise the same or a different combination of polymers as the adhesive polymeric diffusion environment or the non-adhesive polymeric diffusion environment.

In some embodiments, the backing layer includes an additional medicament, such as, for e.g., donepezil (ARICEPT®), rivastigmine (EXCELON®), galantamine (RAZADYNE®), methylphenidate, icopezil, pyridostigmine, edrophonium, neostigmine, physostigmine, Huperzine A, phenserine, tacrine, including, L-type calcium channel blocker selected from amlodipine, felodipine, isradipine, lacidipine, lercanidipine, nicardipine, nifedipine, nimodipine, nitrendipine, nisoldipine, or (+) isopropyl 2-methoxyethyl 4-(2-chloro-3-cyano-phenyl)-1,4-dihydro-2,6-dimethylpyridine-3,5-dicarboxylate, or a combination thereof. In some embodiments, the backing layer functions as a barrier to facilitate a unidirectional flux of the medicament, e.g., memantine, disposed in the reservoir. In another embodiment, the backing layer can serve as an erodible polymer that facilitates absorption of the drug in the tissue. In some embodiments, the backing layer prevents diffusion away from the tissue surface. In such instances, a majority of the medicament, i.e., at least 50%, at least 75%, at least 90% or more, flows towards the contact tissue. In other embodiments, the non-adhesive polymeric environment may circumscribe the boundaries of the adhesive polymeric diffusion environment thereby ensuring that medicament flows toward the target tissue.

The backing layer (e.g., a water-erodible non-adhesive backing layer) can further include at least one water erodible, film-forming polymer. This layer may optionally include a drug. The polymer or polymers can include polyethers and polyalcohols as well as hydrogen bonding cellulosic polymers having either hydroxyalkyl group substitution or hydroxyalkyl group and alkyl group substitution preferably with a moderate to high ratio of hydroxyalkyl to alkyl group. Examples include, but are not limited to, hydroxyethyl cellulose (HEC), hydroxypropyl cellulose (HPC), hydroxypropylmethyl cellulose (HPMC), hydroxyethylmethyl cellulose (HEMC), polyvinyl alcohol (PVA), polyethylene glycol (PEG), polyethylene oxide (PEO), ethylene oxide-propylene oxide co polymers, ethylene oxide-propylene oxide co-polymers, and combinations thereof. The water-erodible non-adhesive backing layer component can optionally be cross-linked.

In certain embodiments, the non-adhesive backing layer is free of cross-linked polymers. In some embodiments, the non-adhesive backing layer is free of polyacrylic acid. While not wishing to be bound by any specific theory, it is estimated that the residence time of the agent is reduced by the absence of said polyacrylic acid. In a preferred embodiment, the water erodible non-adhesive backing layer includes hydroxyethyl cellulose and hydroxypropyl cellulose.

The transdermal devices described herein can include ingredients that are employed to, at least in part, provide a desired residence time. In some embodiments, this is a result of the selection of the appropriate backing layer formulation, providing a slower rate of erosion of the backing layer. Thus, the non-adhesive backing layer is further modified to render controlled erodability which can be accomplished by coating the backing layer film with a more hydrophobic polymer selected from a group of FDA approved EUDRAGIT™ polymers, ethyl cellulose, cellulose acetate phthalate, and hydroxyl propyl methyl cellulose phthalate, that are approved for use in other pharmaceutical dosage forms. Other hydrophobic polymers may be used, alone or in combination with other hydrophobic or hydrophilic polymers, provided that the layer derived from these polymers or combination of polymers erodes in a moist environment. Dissolution characteristics may be adjusted to modify the residence time and the release profile of a drug when included in the backing layer.

In some embodiments, other additional layers in the transdermal devices comprise any of the aforementioned materials. In certain embodiments, the additional layers, e.g., support layers, may also contain a plasticizing agent, such as propylene glycol, polyethylene glycol, or glycerin in a small amount, 0 to 15% by weight, in order to improve the "flexibility" of this layer in the tissue and to adjust the erosion rate of the device, e.g., particularly in skin containing high density of sudoriparous glands. In addition, humectants such as hyaluronic acid, glycolic acid, and other alpha hydroxyl acids can also be added to improve the "softness" and "feel" of the device. Finally, colors and opacifiers may be added to help distinguish the resulting non-adhesive backing layer from the mucoadhesive polymeric diffusion environment. Some opacifers include titanium dioxide, zinc oxide, zirconium silicate, etc.

The transdermal device can also optionally include one or more of pharmaceutically acceptable dissolution-rate-modifying agents, pharmaceutically acceptable disintegration aids (e.g., polyethylene glycol, dextran, polycarbophil, carboxymethyl cellulose, or poloxamers), pharmaceutically acceptable plasticizers, pharmaceutically acceptable coloring agents (e.g., FD&C Blue #1), pharmaceutically acceptable opacifiers (e.g., titanium dioxide), pharmaceutically acceptable anti-oxidants (e.g., tocopherol acetate), pharmaceutically acceptable system forming enhancers (e.g., polyvinyl alcohol or polyvinyl pyrrolidone), pharmaceutically acceptable preservatives, flavorants (e.g., saccharin and peppermint), neutralizing agents (e.g., sodium hydroxide), buffering agents (e.g., monobasic, or tribasic sodium phosphate), or combinations thereof. Preferably, these components are individually present at no more than about 1% of the final weight of the device, but the amount may vary depending on the other components.

In some embodiments, the non-adhesive polymeric diffusion environment, e.g., the backing layer, is a buffered environment. In some embodiments the pH of the backing layer is between 5.0 and 9.0, more specifically, between 6.2 and 8.5, and even more specifically, between 7.0 and 8.0. In one embodiment, the pH of the backing layer is about 7.4. It is to be understood that all values and ranges between these values and ranges are meant to be encompassed.

The pH of the backing layer can be adjusted and/or maintained by methods including, but not limited to, the use of buffering agents, or by adjusting the composition of the device. In some embodiments, the properties of the polymeric diffusion environment are influenced by its buffering capacity.

Fabrication of a transdermal delivery system is routinely done by skilled artisans and involves casting or extruding each of the adhesive layers onto a suitable film such as a release liner or onto another layer of the transdermal delivery system, and drying if needed to remove solvents and/or volatile compounds. Layers of the transdermal delivery system can be laminated together to form the final system.

Transdermal delivery systems and drug reservoir adhesive matrices were prepared to illustrate the embodiments described herein. Examples 1-2 set forth exemplary compositions and delivery systems. As described in Example 1, a transdermal delivery system is prepared comprising a drug reservoir layer and a contact adhesive layer with a rate controlling membrane layer situated between the drug reservoir and the contact adhesive layers, as depicted in FIG. 1A. A drug reservoir in the form of a solid monolithic adhesive reservoir is prepared using an acrylic acid/vinyl acetate copolymer adhesive and cross-linked polyvinylpyrrolidone (PVP-CLM), along with the named dissolving agents, carriers and optionally permeation enhancers (Table 1). The drug reservoir contains approximately 25 wt % memantine hydrochloride and 9.73 wt % sodium bicarbonate, to generate in situ memantine base. A contact adhesive layer containing higher alcohol and biocompatible polymer is synthesized. In a second variant, the contact adhesive contained the higher alcohol and biocompatible polymer, along with dispersive silica. To control the diffusional release of memantine base from the drug reservoir, a rate-controlling membrane may be introduced in between the drug reservoir and the contact adhesive.

TABLE 1

Transdermal delivery systems, with two contact adhesive formulations

| COMPONENTS | Drug Reservoir Dry Composition (%) | Contact Adhesive #1 Dry Composition (%) | Contact Adhesive #2 Dry Composition (%) |
|---|---|---|---|
| Memantine HCl | 25% | 0 | 0 |
| Sodium bicarbonate | 9.73% | 0 | 0 |
| Octyldodecanol | 10% | 10% | 10% |
| Glycerol | 10% | 0 | 0 |
| fumed silica (AEROSIL ® 200) | 0 | 0 | 7% |
| crosslinked polyvinylpyrrolidone (KOLLIDON ® CL-M) | 15% | 20% | 0 |
| acrylic acid/vinyl acetate copolymer (DURO-TAK ® 387/87-2287) | 30.3% | 0 | 0 |
| Polyisobutylene/polybutene | 0 | 70% | 83% |
| Total | 100% | 100% | 100% |

As described in Example 1, transdermal delivery systems are prepared and are comprised of a drug reservoir and a skin contact adhesive layer separated by an intermediate layer. The drug reservoir in the exemplary systems comprises the copolymer acrylic acid/vinyl acetate and cross-linked polyvinylpyrrolidone (KOLLIDON-CLM). These base materials are mixed with the named carriers and dissolving agents, memantine hydrochloride and sodium bicarbonate (Table 2). The drug reservoir contains approximately 25 wt % memantine hydrochloride and 9.73 wt % sodium bicarbonate, to generate in situ memantine base. The skin contact adhesive layer contains a higher alcohol and biocompatible polymer.

TABLE 2

Transdermal delivery system

| | Drug Reservoir Dry Composition (%) | Contact Adhesive Dry Composition (%) |
|---|---|---|
| Memantine HCl | 25% | 0 |
| Sodium bicarbonate | 9.7% | 0 |
| Octyldodecanol | 7% | 10% |
| Glycerol | 10% | 0 |
| crosslinked polyvinylpyrrolidone (KOLLIDON ® CL-M) | 15% | 20% |
| acrylic acid/vinyl acetate copolymer (DURO-TAK ® 387/87-2287) | 33.3% | 0 |
| polyisobutylene/polybutene | 0 | 70% |
| Total | 100% | 100% |

Figure 2:
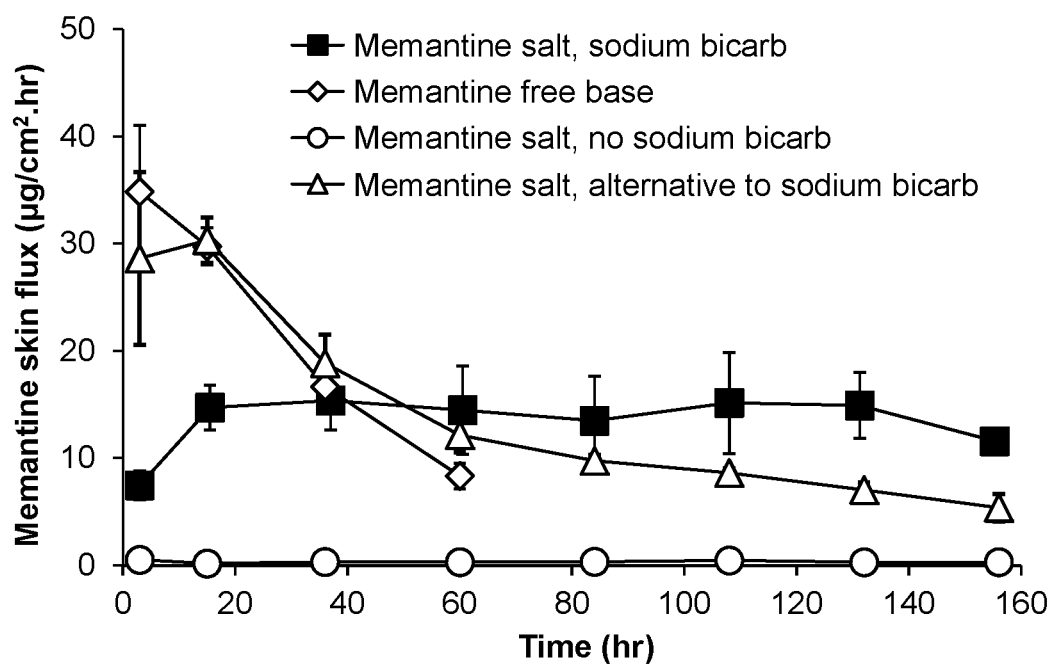
FIG. 2 is a graph of average skin flux for memantine transdermal delivery devices, in $\mu g/cm^2 \cdot hr$, in vitro as a function of time, in hours, in an in vitro skin permeation test.

A memantine transdermal system was prepared as described in Example 2 to demonstrate the delivery of an active agent formulated from an amine salt form of the active agent and an amphoteric inorganic base compound. The memantine transdermal system was evaluated in vitro by measuring release of memantine from the system and across human skin and the results are shown in FIG. 2 (squares). About 18 hours after application of the transdermal system to the skin, a steady-state flux rate of between about 12-15 µg/cm²-hr was achieved. The flux rate remained steady for about 6.5 days before decreasing. Accordingly, in one embodiment, a transdermal delivery system for delivery of a base form of an active agent is prepared from an amine salt form of the active agent and sodium bicarbonate, to provide a skin flux rate or permeation rate that is therapeutic for a period of at least about 3 days or 5 days or 7 days (or from 3-7 days). In one embodiment, the steady state in vitro skin flux rate remains within 15%, 20%, 25%, or 30% for a period of at least about 3 days or 5 days or 7 days (or from 3-7 days). That is, the in vitro skin flux measured at time point y varies from an in vitro skin flux measured at an earlier adjacent time point x, where x and y are each time points within a 3 day, 5 day, or 7 day measurement period, by less than 15%, 20%, 25% or 30%.

Comparative examples were also conducted to illustrate the inventive composition, system and methods described herein. FIG. 2 illustrates that adhesive compositions (transdermal systems) prepared with the free base form of the drug (diamond), with the amine salt form of drug but without sodium bicarbonate (circle) or a salt form of an amine drug and an amphoteric inorganic base compound, but where the pKa of the amphoteric inorganic base compound is not lower than that of the amine salt form of the active agent but is higher (triangle). In these comparative examples, the in vitro skin flux of the drug is insufficient for therapy.

Kits/Articles Containing the Compositions

In certain aspects, kits comprising the systems comprising the memantine compound with a carrier, optionally together with instructions for formulating a patch or suppository comprising the memantine compound are described herein. The components of the kit, e.g., the systems containing the memantine compound and the carrier, optionally together with other ingredients, e.g., gelling agents, emollients, surfactants, humectants, viscosity enhancers, emulsifiers, etc., in one or more compartments. The kits may optionally comprise instructions for formulating the systems and/or using the components, either individually or together, in the treatment of the CNS diseases.

In a related embodiment, the present kits comprise an article (e.g., an intradermal, a subcutaneous, or a transdermal patch or an implant) comprising the aforementioned compositions. Alternately, the kits may include the individual components, e.g., the compositions and the articles for administration of the compositions, separately, optionally together with secondary information for assembling and/or using the components.

In some embodiments, delivery systems that are filled with single or multi-dose amounts of the compositions are provided. Preferably, the device is filled with one single dose of the compositions. In a preferred embodiment, the reservoir holding the pharmaceutical composition and its sealing means are sterilizable, most preferably, at least parts of the delivery systems that are in contact with the composition is constructed and assembled in a configuration that can be sterilized. Delivery systems with one or more unit-dose(s) can be sterilized either before or after packaging, employing methods and technology that are well known in the art. Individual delivery systems can be packaged, sterilized and shipped; alternatively, entire shipping and storage packages can be sterilized at once, and the devices removed individually for dispensing, without affecting the sterility of the remaining units.

Methods of Treatment

In other aspects, methods of treating a disease, condition, and/or disorder by transdermal administration of at least one active agent by the transdermal compositions, devices, and/or systems described herein.

In some embodiments, therapy of CNS disorders using the compositions and the delivery systems are described. Examples of CNS disorders include, but are not limited to, dementia (e.g., Alzheimer's disease, Parkinson's disease, Picks disease, fronto-temporal dementia, vascular dementia, normal pressure hydrocephalus, Huntington's disease (HD), and mild cognitive impairment (MCI)), neuro-related conditions, dementia-related conditions, such as epilepsy, seizure disorders, acute pain, chronic pain, chronic neuropathic pain may be treated using the combinations and methods described herein. Epileptic conditions include complex partial, simple partial, partials with secondary generalization, generalized-including absence, grand mal (tonic clonic), tonic, atonic, myoclonic, neonatal, and infantile spasms. Additional specific epilepsy syndromes are juvenile myoclonic epilepsy, Lennox-Gastaut, mesial temporal lobe epilepsy, nocturnal frontal lobe epilepsy, progressive epilepsy with mental retardation, and progressive myoclonic epilepsy. The combinations are also useful for the treatment and prevention of pain caused by disorders including cerebrovascular disease, motor neuron diseases (e.g., ALS, Spinal motor atrophies, Tay-Sach's, Sandoff disease, familial spastic paraplegia), neurodegenerative diseases (e.g., familial Alzheimer's disease, prion-related diseases, cerebellar ataxia, Friedrich's ataxia, SCA, Wilson's disease, RP, ALS, Adrenoleukodystrophy, Menke's Sx, cerebral autosomal dominant arteriopathy with subcortical infarcts (CADASIL); spinal muscular atrophy, familial ALS, muscular dystrophies, Charcot Marie Tooth diseases, neurofibromatosis, von-Hippel Lindau, Fragile X, spastic paraplegia, psychiatric disorders (e.g., panic syndrome, general anxiety disorder, phobic syndromes of all types, mania, manic depressive illness, hypomania, unipolar depression, depression, stress disorders, PTSD, somatoform disorders, personality disorders, psychosis, and schizophrenia), and drug dependence (e.g., alcohol, psychostimulants (e.g., crack, cocaine, speed, meth), opioids, and nicotine), Tuberous sclerosis, and Wardenburg syndrome), strokes (e.g., thrombotic, embolic, thromboembolic, hemmorhagic, venoconstrictive, and venous), movement disorders (e.g., PD, dystonias, benign essential tremor, tardive dystonia, tardive dyskinesia, and Tourette's syndrome), ataxic syndromes, disorders of the sympathetic nervous system (e.g., Shy Drager, Olivopontoicerebellar degeneration, striatonigral degenration, Parkinson's disease (PD), Huntington's disease (HD), Gullian Barre, causalgia, complex regional pain syndrome types I and II, diabetic neuropathy, and alcoholic neuropathy), Cranial nerve disorders (e.g., Trigeminal neuropathy, trigeminal neuralgia, Menier's syndrome, glossopharangela neuralgia, dysphagia, dysphonia, and cranial nerve palsies), myelopethies, traumatic brain and spinal cord injury, radiation brain injury, multiple sclerosis, Post-menengitis syndrome, prion diseases, myelities, radiculitis, neuropathies (e.g., Guillian-Barre, diabetes associated with dysproteinemias, transthyretin-induced neuropathies, neuropathy associated with HIV, neuropathy associated with Lyme disease, neuropathy associated with herpes zoster, carpal tunnel syndrome, tarsal tunnel syndrome, amyloid-induced neuropathies, leprous neuropathy, Bell's palsy, compression neuropathies, sarcoidosis-induced neuropathy, polyneuritis cranialis, heavy metal induced neuropathy, transition metal-induced neuropathy, drug-induced neuropathy), axonic brain damage, encephalopathies, and chronic fatigue syndrome. All of the above disorders may be treated with the systems and methods described herein.

The terms "treatment," "therapy," "therapeutic" and the like, as used herein, encompass any course of medical intervention aimed at a pathologic condition, and includes not only permanent cure of a disease, but prevention of disease, control or even steps taken to mitigate a disease or disease symptoms. For instance, in reference to methods of treating a disorder, such as Alzheimer's disease, the embodiment, generally includes the administration of a compound or composition which reduces the frequency of, or delays the onset of, symptoms of a medical condition (e.g., Alzheimer's disease) in a subject relative to a subject not receiving the compound or composition. This can include reversing, reducing, or arresting the symptoms, clinical signs, and underlying pathology of a condition in a manner to improve or stabilize a subject's condition (e.g., regression of mental facilities).

The compositions of the present disclosure can comprise, consist essentially of, or consist of, the components disclosed.

In one embodiment, the therapeutic embodiments are carried out by contacting a tissue of a subject, e.g., skin tissue, with the transdermal delivery system. As defined herein, "contacting" means that the composition comprising the active ingredient is introduced into a sample containing a target, e.g., cell target, in a test tube, flask, tissue culture, chip, array, plate, microplate, capillary, or the like, and incubated at a temperature and time sufficient to permit binding of the composition to the target. Methods for contacting the samples with the compound or other specific binding components are known to those skilled in the art and may be selected depending on the type of assay protocol to be run. Incubation methods are also standard and are known to those skilled in the art. In another embodiment, the term "contacting" means that the compound used is introduced into a patient or a subject for the treatment of a CNS disorder, e.g., Alzheimer's disease or dementia, and other related diseases and conditions, and the compound is allowed to come in contact with the patient or subject in vivo.

In another embodiment, the therapeutic embodiments are carried out by administering the compositions and kits to a subject, e.g., a patient suffering from a CNS disorder such as Alzheimer's disease and/or dementia. The term "administering" means applying as a remedy, such as by the placement of a drug in a manner in which such drug would be received, e.g., transdermally, and be effective in carrying out its intended purpose.

A "subject" or "patient" in whom administration of the therapeutic compound is an effective therapeutic regimen for a disease or disorder is preferably a human, but can be any animal, including a laboratory animal in the context of a trial or screening or activity experiment. Thus, as can be readily appreciated by one of ordinary skill in the art, the methods, compounds and compositions are particularly suited to administration to any animal, particularly a mammal, and including, but by no means limited to, humans, domestic animals, such as feline or canine subjects, farm animals, such as but not limited to bovine, equine, caprine, ovine, and porcine subjects, wild animals (whether in the wild or in a zoological garden), research animals, such as mice, rats, rabbits, goats, sheep, pigs, dogs, cats, etc., avian species, such as chickens, turkeys, songbirds, etc., e.g., for veterinary medical use.

The term "therapeutically effective amount" as used herein refers to the amount of an active agent that is nontoxic but sufficient to provide the desired therapeutic effect. The amount that is "effective" will vary from subject to subject, depending on the age and general condition of the individual, the particular active agent or agents, and the like as known to those skilled in the art.

Treatment of a subject with the combination may be monitored using methods known in the art. See, e.g., Forchetti et al., "Treating Patients with Moderate to Severe Alzheimer's Disease: Implications of Recent Pharmacologic Studies." *Prim Care Companion J Clin Psychiatry,* 7(4): 155-161, 2005 (PMID: 16163398). The efficacy of treatment using the combination is preferably evaluated by examining the subject's symptoms in a quantitative way, e.g., by noting a decrease in the frequency of adverse symptoms, behaviors, or attacks, or an increase in the time for sustained worsening of symptoms. In a successful treatment, the subject's status will have improved (i.e., frequency of relapses will have decreased, or the time to sustained progression will have increased). The term "treating" is used herein, for instance, in reference to methods of treating a disorder, such as Alzheimer's disease, and generally includes the administration of a compound or composition which reduces the frequency of, or delays the onset of, symptoms of a medical condition (e.g., Alzheimer's disease) in a subject relative to a subject not receiving the compound or composition. This can include reversing, reducing, or arresting the symptoms, clinical signs, and underlying pathology of a condition in a manner to improve or stabilize a subject's condition (e.g., regression of mental facilities).

Based on the exemplary compositions and transdermal delivery systems (also referred to as transdermal devices or devices) described herein, a method for treating a suitable condition with memantine is provided. In embodiments, compositions and devices comprising memantine are useful for treating, delaying progression, delaying onset, slowing progression, preventing, providing remission, and improvement in symptoms of cognitive disorders or disease are provided herein. In embodiments, compositions and devices comprising memantine are provided for maintaining mental function including, but not limited to a least one of maintaining thinking, memory, speaking skills as well as managing or moderating one or more behavioral symptoms of a cognitive disorder or disease. In embodiments, the cognitive disorder is Alzheimer's disease. In particular embodiments, the cognitive disorder is Alzheimer's type dementia. In embodiments, compositions and devices comprising memantine are provided for use in treating, etc. mild, moderate, or severe Alzheimer's disease.

Treatment of Alzheimer's Disease and Symptoms Thereof

Alzheimer's disease is the most common cause of senile dementia and is characterized by cognitive deficits related to degeneration of cholinergic neurons. Alzheimer's affects 6-8% of people over the age of 65 and nearly 30% of people over the age of 85 (Sozio et al., *Neurophsychiatric Disease and Treatment,* 2012, 8:361-368), involving the loss of cognitive functioning and behavioral abilities. The causes of Alzheimer's disease are not yet fully understood. As Alzheimer's disease is associated with reduced levels of several cerebral neurotransmitters including acetylcholine (Ach), current treatment includes administering cholinesterase inhibitors. Cholinesterase inhibitors reduce the hydrolysis of acetylcholine in the synaptic cleft by inhibiting cholinesterase and/or butyrylcholinesterase, which increases acetylcholine levels resulting in improved neurotransmission (Id.).

The transdermal devices described herein may be designed for long term use and/or continuous administration of the active agent. The FDA has approved doses of memantine of 2 mg, 5 mg, 7 mg, 10 mg, 14 mg, 21 mg, and 28 mg. It will be appreciated that the total dose of the active agent per transdermal device will be determined by the size of the device and the loading of the active agent within the adhesive matrix. In an embodiment, the active agent is memantine in free base form. Lower drug loading of memantine base may be effective as compared to the salt form (e.g. memantine hydrochloride). The ability to include lower drug loading to achieve efficacy results in a lower profile for the device (thinner) and/or smaller size, both of which are desirable to reduce discomfort. In some embodiments, the application period for the transdermal device is between about 1-10 days, 1-7 days, 1-5 days, 1-2 days, 3-10 days, 3-7 days, 3-5 days, 5-10 days, and 5-7 days inclusive. In some embodiments, the active agent is released from the adhesive matrix as a continuous and/or sustained release over the application period.

In some embodiments, the transdermal delivery systems may be administered with other pharmaceutically active materials for combination therapy, e.g., donepezil (ARICEPT®), rivastigmine (EXCELON®), galantamine (RAZADYNE®), methylphenidate, icopezil, pyridostigmine, edrophonium, neostigmine, physostigmine, Huperzine A, phenserine, tacrine, including, L-type calcium channel blocker selected from amlodipine, felodipine, isradipine, lacidipine, lercanidipine, nicardipine, nifedipine, nimodipine, nitrendipine, nisoldipine, or (+) isopropyl 2-methoxyethyl 4-(2-chloro-3-cyano-phenyl)-1,4-dihydro-2,6-dimethylpyridine-3,5-dicarboxylate, or a combination thereof. The FDA has approved the following daily dosages: (a) donepezil: 5 mg, 10 mg, and 23 mg; (b) rivastigmine: 1.5 mg, 2.0 mg, 3.0 mg, 4.5 mg, 4.6 mg, 6.0 mg, 9.0 mg, 9.5 mg, and 13.3 mg; (c) methylphenidate: 2.5 mg, 5 mg, 10 mg, 15 mg, 18 mg, 20 mg, 27 mg, 30 mg, 36 mg, 40 mg, 50 mg, 54 mg, and 60 mg; (d) galantamine: 4 mg, 8 mg, 12 mg, 4 mg/mL, 16 mg, 24 mg; (e) pyridostigmine: 5 mg/mL, 180 mg, 60 mg, 60 mg/5 mL; (f) edrophonium: 10 mg/mL; (g) neostigmine/physostigmine: 0.5-2.0 mg (intravenous; intraperitoneal); (h) L-type calcium channel blockers, e.g., isradipine: 5-20 mg/day.

A method for delivering memantine base transdermally to a subject is provided. In the method a transdermal delivery system is applied to the skin, and upon application of the transdermal delivery system to the skin of a subject, transdermal delivery of the memantine base occurs, to provide a systemic blood concentration of the agent (or a metabolite) that is bioequivalent to administration of the therapeutic agent orally. As discussed below, bioequivalency is established by (a) a 90% confidence interval of the relative mean $C_{max}$ and AUC of the therapeutic agent administered from the transdermal delivery system and via oral delivery are between 0.80 and 1.25, or (b) a 90% confidence interval of the ratios for AUC and $C_{max}$ of the therapeutic agent administered from the transdermal delivery system and via oral delivery are between 0.80 and 1.25.

Standard pharmacokinetic (PK) parameters routinely used to assess the behavior of a dosage form in vivo (in other words when administered to an animal or human subject) include $C_{max}$ (peak concentration of drug in blood plasma), $T_{max}$ (the time at which peak drug concentration is achieved) and AUC (the area under the plasma concentration vs time curve). Methods for determining and assessing these parameters are well known in the art. The desirable pharmacokinetic profile of the transdermal delivery systems described herein comprise but are not limited to: (1) a $C_{max}$ for transdermally delivered form of the memantine when assayed in the plasma of a mammalian subject following administration, that is bioequivalent to the $C_{max}$ or an orally delivered or an intravenously delivered form of the drug, administered at the same dosage; and/or (2) an AUC for transdermally delivered form of memantine when assayed in the plasma of a mammalian subject following administration, that is preferably bioequivalent to the AUC for an orally delivered or an intravenously delivered form of the drug, administered at the same dosage; and/or (3) a $T_{max}$ for transdermally delivered form of memantine when assayed in the plasma of a mammalian subject following administration, that is within about 80-125% of the $T_{max}$ for an orally delivered or an intravenously delivered form of the drug, administered at the same dosage. Preferably the transdermal delivery system exhibits a PK profile having a combination of two or more of the features (1), (2) and/or (3) in the preceding sentence. Alternatively, the transdermal delivery system exhibits a PK profile having features (1) and/or (2).

In the field of pharmaceutical development the term "bioequivalence" will be readily understood and appreciated by the person skilled in the art. Various regulatory authorities have strict criteria and tests for assessing whether or not two drug products are bioequivalent. These criteria and tests are commonly used throughout the pharmaceutical industry and the assessment of bioequivalence is recognized as a standard form of activity in drug development programs where the characteristics and performance of one product are being compared to those of another product. Indeed in seeking approval to market certain types of products (e.g. those evaluated under the FDA's "Abbreviated New Drug Application" procedure), it is a requirement that the follow-on product be shown to be bioequivalent to a reference product.

In one embodiment, the method encompasses providing and/or administering a transdermal delivery system comprising memantine base to a subject in a fasted state is bioequivalent to administration of the agent (in base or salt form) orally or intravenously to a subject also in a fasted state, in particular as defined by $C_{max}$ and AUC guidelines given by the U.S. Food and Drug Administration and the corresponding European regulatory agency (EMEA). Under U.S. FDA and Europe's EMEA guidelines, two products or methods are bioequivalent if the 90% Confidence Intervals (CI) for AUC and $C_{max}$ are between 0.80 to 1.25 ($T_{max}$ measurements are not relevant to bioequivalence for regulatory purposes). Europe's EMEA previously used a different standard, which required a 90% CI for AUC between 0.80 to 1.25 and a 90% CI for $C_{max}$ between 0.70 to 1.43. Methods for determining $C_{max}$ and AUC are well known in the art.

Accordingly, in one embodiment, a method for delivering memantine base to a subject is provided. The method comprises providing a transdermal delivery system comprised of memantine, and administering or instructing to administer the transdermal delivery system to the skin of a subject. The method achieves transdermal delivery of memantine at steady state that is bioequivalent to administration of the therapeutic agent orally, wherein bioequivalency is established by (a) a 90% confidence interval of the relative mean Cmax and AUC of the therapeutic agent administered from the transdermal delivery system and via oral delivery between 0.70 to 1.43 or between 0.80 and 1.25, or (b) a 90% confidence interval of the geometric mean ratios for AUC and Cmax of the therapeutic agent administered from the transdermal delivery system and via oral delivery between 0.70 to 1.43 or between 0.80 and 1.25.

EXAMPLES

The following examples are illustrative in nature and are in no way intended to be limiting.

Example 1

Memantine Transdermal Delivery System

A transdermal delivery system comprising memantine is prepared as follows.

Preparation of Drug Reservoir:

A memantine salt and an alkaline salt are dissolved in a mixture of ethyl acetate, isopropyl alcohol, propylene glycol, and levulinic acid, to form a clear solution. In one variation, fumed silica (AEROSIL® 200P) is added and the mixture is homogenized. To the homogenous mixture, a copolymer of acrylic acid/vinyl acetate (DURO-TAK® 387-2287) is added and mixed until the mixture becomes homogenous.

The adhesive formulation mixture is coated on a siliconized polyethylene terephthalate liner and dried in a Werner Mathis coater at 60° C. for 8 minutes to yield a dry adhesive layer.

A transdermal delivery system is fabricated using two of the dry adhesive layers sandwiched together with a non-woven polyester fabric between the two adhesive layers. Then, coated polyethylene terephthalate liner is replaced with a backing film.

Preparation of Contact Adhesive:

Octyldodecanol, crosslinked, micronized polyvinylpyrrolidone (KOLLIDON® CL-M), and an optional solvent are mixed and the mixture is homogenized. To the homogenized mixture, polyisobutylene/polybutene (PIB/PB) is added and mixed well. The polyisobutylene/polybutene adhesive solution was a mixture of 10% polyisobutylene known as Oppanol® B-100, 50% polyisobutylene known as Oppanol® B-12 and 40% polybutene known as Indopol® H 1900. The wet adhesive formulation is coated on a release liner and dried.

Lamination and Die-Cut:

A rate controlling membrane (CELGARD® 2400) or a non-woven membrane layer (Reemay® 2250) is laminated on the adhesive side of the drug reservoir. Then the contact adhesive is laminated on top of the rate controlling membrane laminated with the drug reservoir. The release liner on the drug reservoir side is replaced and laminated with a backing film.

Transdermal delivery systems are then die-cut from the laminate.

Example 2

Memantine Salt Transdermal Formulation with Sodium Bicarbonate

Preparation of Drug-in-Adhesive:

An amount of 2.0 g of glycerine and 2.0 g of octyl dodecanol were mixed with a mixture of 29.35 g of ethyl acetate and 1.86 g of isopropyl alcohol. In the solution, 5.0 g of memantine hydrochloride and 1.95 g of sodium bicarbonate were dispersed by stirring. To the dispersion, 3.0 g of cross-linked polyvinylpyrrolidone (KOLLIDON® CL-M) was added and homogenized using a Silverson mixer homogenizer. To the homogenized drug/cross-linked polyvinylpyrrolidone dispersion, 11.99 g of acrylate copolymer (DURO-TAK® 387-2287, solid content 50.5%) was added and mixed well. The wet adhesive formulation was coated on a release liner and dried using a Werner Mathis coater to get a dry coat weight of 15 mg/cm$^2$.

Preparation of Contact Adhesive:

An amount of 2.0 g of octyl dodecanol was mixed with 20.67 g of n-heptane. After addition of 4.00 g of cross-linked polyvinylpyrrolidone (KOLLIDON® CL-M) to the solution, the mixture was homogenized using a Silverson mixer homogenizer. To the homogenized mixture, an amount of 23.33 g of polyisobutylene/polybutylene (60/40) adhesive solution (solid content 60%) was added and mixed well. The polyisobutylene/polybutene adhesive solution was a mixture of 10% polyisobutylene known as Oppanol® B-100, 50% polyisobutylene known as Oppanol® B-12 and 40% polybutene known as Indopol® H 1900. The wet adhesive formulation was coated on a release liner and dried to give a dry coat weight of 5 mg/cm$^2$.

Lamination and Die-Cut:

A polypropylene microporous membrane (Celgard® 2400) was laminated between the drug-in-adhesive layer and the contact adhesive layer. Before the microporous membrane was laminated, it was pretreated by coating it with octyl dodecanol to fill the pores of the membrane. The release liner on the drug-in-adhesive side was replaced and laminated with a backing, 3M SCOTCHPAK® 1012. The final five layer laminate was die-cut into patches. FIG. 4 depicts the design of the patch.

Evaluation of In Vitro Skin Flux:

Dermatomed human cadaver skin was obtained from a skin bank and frozen until ready for use. The skin was placed in water at 60° C. for 1-2 mins minute after thawing and the epidermis carefully separated from dermis. The epidermis was either used immediately or wrapped and frozen for later use.

In vitro skin flux studies were performed using a Franz type diffusion cell with an active diffusion area of 0.64 cm$^2$. The epidermis was mounted between the donor and receptor compartments of the diffusion cell. The transdermal delivery system was placed over the skin and the two compartments were clamped tight together.

The receptor compartment was filled with 0.01 M phosphate buffer, pH=6.5, containing 0.01% gentamicin. The solution in the receptor compartment was continually stirred using a magnetic stirring bar in the receptor compartment. The temperature was maintained at 32±0.5° C. Samples were drawn from the receptor solution at periodic intervals and the receptor solution was replaced with fresh phosphate buffers solution. Drug content in the samples was analyzed using LCMS for memantine.

The flux profile results are shown in FIG. 2 (squares). The flux in this example is relatively high and remains relatively constant over 7 days.

Example 3

In Vivo Administration of Memantine with Transdermal Delivery System

Transdermal delivery systems comprising memantine are prepared as described in Example 1. Human subjects are randomized into two groups for treatment with a transdermal delivery system or with orally administered memantine (NAMENDA®), 7 mg taken on day one and on day 7 of the study. The transdermal delivery system is applied to the skin and worn for one week and then removed. Blood samples are taken daily from the subjects treated with the transdermal delivery system. Blood samples were taken at frequent hour intervals on day 1 and day 7 in the group treated with orally delivered memantine, and again on days 8, 10, 12 and 14. Mean plasma concentration of memantine in the treatment groups are measured.

While a number of exemplary aspects and embodiments have been discussed above, those of skill in the art will recognize certain modifications, permutations, additions and sub-combinations thereof. It is therefore intended that the following appended claims and claims hereafter introduced are interpreted to include all such modifications, permutations, additions and sub-combinations as are within their true spirit and scope.

For convenience, certain terms employed in the specification, examples and claims are collected here. Unless defined otherwise, all technical and scientific terms used in this disclosure have the same meanings as commonly understood by one of ordinary skill in the art to which this disclosure belongs.

All percentages, parts and ratios are based upon the total weight of the topical compositions and all measurements made are at about 25° C., unless otherwise specified.

By reserving the right to proviso out or exclude any individual members of any such group, including any sub-ranges or combinations of sub-ranges within the group, that can be claimed according to a range or in any similar manner, less than the full measure of this disclosure can be claimed for any reason. Further, by reserving the right to proviso out or exclude any individual substituents, analogs, compounds, ligands, structures, or groups thereof, or any members of a claimed group, less than the full measure of this disclosure can be claimed for any reason.

Throughout this disclosure, various patents, patent applications and publications are referenced. The disclosures of these patents, patent applications, accessioned information (e.g., as identified by PUBMED or PUBCHEM accession numbers) and publications in their entireties are incorporated into this disclosure by reference in order to more fully describe the state of the art as known to those skilled therein as of the date of this disclosure. This disclosure will govern in the instance that there is any inconsistency between the patents, patent applications and publications cited and this disclosure.

It is claimed:

1. A composition, comprising: a drug reservoir consisting essentially of a salt of memantine and an alkaline salt; a permeation enhancer; a hydrophilic solvent carrier; a cross-linked polyvinylpyrrolidone; and an acrylate copolymer, wherein, after application of the composition to the skin of a subject, memantine base is generated in situ by reaction of the salt of memantine and the alkaline salt.

2. The composition of claim 1, wherein the hydrophilic solvent carrier is glycerol.

3. The composition of claim 1, wherein the permeation enhancer is a higher alcohol selected from the group consisting of lauryl alcohol, isostearyl alcohol, octyldodecanol, and oleyl alcohol.

4. The composition of claim 1, wherein the salt of memantine is memantine hydrochloride and the alkaline salt is selected from the group consisting of sodium acetate, sodium borate, sodium metaborate, sodium carbonate, sodium bicarbonate, potassium carbonate, potassium bicarbonate, potassium citrate, potassium acetate, sodium phosphate, potassium phosphate, disodium hydrogen phosphate, sodium oxylate, sodium succinate, sodium citrate, and sodium salicylate.

5. The composition of claim 1, further comprising a skin contact adhesive comprised of polyisobutylene (PIB), polybutylene, or a mixture thereof.

6. The composition of claim 5, wherein the skin contact adhesive comprises (i) about 5-15 wt % octyldodecanol; (ii) a mixture of polyisobutylene and polybutylene; and optionally (iii) about 10-30 wt % cross-linked PVP.

7. The composition of claim 5, wherein the skin contact adhesive comprises, (i) about 8-12 wt % octyldodecanol; (ii) about 65-90 wt % of a mixture of polyisobutylene and polybutylene; and optionally (iii) about 15-25 wt % cross-linked PVP.

8. The composition of claim 1, wherein memantine base is generated in situ in the drug reservoir over a 3-5 day period.

9. The composition of claim 1, wherein the salt of memantine is memantine hydrochloride and the alkaline salt is sodium bicarbonate.

10. The composition of claim 9, wherein the drug reservoir comprises a molar amount of memantine hydrochloride and an equimolar or less than less than equimolar amount of sodium bicarbonate.

11. The composition of claim 10, wherein the drug reservoir comprises between about 10-30 wt % memantine hydrochloride.

12. The composition of claim 10, wherein the drug reservoir comprises between about 22-27 wt % memantine hydrochloride.

13. The composition of claim 10, wherein the drug reservoir comprises between about 5-15 wt % sodium bicarbonate.

14. A composition, comprising: a drug reservoir consisting essentially of
   (a) between about 10-30 wt % memantine HCl and between about 5-15 wt % sodium bicarbonate;
   (b) about 5-15 wt % octyldodecanol;
   (c) about 5-15 wt % glycerol;
   (d) about 10-30 wt % crosslinked polyvinylpyrrolidone; and
   (e) about 20-50 wt % acrylate polymer, wherein, after application of the composition to the skin of a subject, memantine base is generated in situ by reaction of the memantine HCl and the sodium bicarbonate.

15. A method for delivering memantine to a subject in need thereof, comprising:
   administering the composition of claim 1 to the skin of a human subject, whereby said administering achieves transdermal delivery of memantine base to the subject.

16. The method of claim 15, wherein the subject is suffering from or has been diagnosed with a CNS disorder.

17. The method of claim 16, wherein the CNS disorder is Alzheimer's disease.

* * * * *